(12) United States Patent
Li et al.

(10) Patent No.: US 12,367,969 B2
(45) Date of Patent: Jul. 22, 2025

(54) INTELLIGENT HEALTHCARE MANAGEMENT SYSTEM, INTELLIGENT HEALTHCARE MANAGEMENT METHOD, AND COMPUTER-PROGRAM PRODUCT

(71) Applicant: BOE Technology Group Co., Ltd., Beijing (CN)

(72) Inventors: Xinran Li, Beijing (CN); Yanyang Hu, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 0 days.

(21) Appl. No.: 17/761,185

(22) PCT Filed: Jun. 17, 2021

(86) PCT No.: PCT/CN2021/100698
§ 371 (c)(1),
(2) Date: Mar. 16, 2022

(87) PCT Pub. No.: WO2022/261903
PCT Pub. Date: Dec. 22, 2022

(65) Prior Publication Data
US 2024/0047048 A1 Feb. 8, 2024

(51) Int. Cl.
*G16H 40/20* (2018.01)
(52) U.S. Cl.
CPC .................. *G16H 40/20* (2018.01)
(58) Field of Classification Search
CPC ........ G16H 10/20; G16H 10/40; G16H 10/60; G16H 10/65; G16H 20/10; G16H 20/13;
(Continued)

(56) References Cited

U.S. PATENT DOCUMENTS 11,276,001 B1 * 3/2022 Sutherland ............. G06V 10/95
2008/0161661 A1 7/2008 Gizewski
(Continued)

FOREIGN PATENT DOCUMENTS

CN 102567611 A 7/2012
CN 102647369 A 8/2012
(Continued)

OTHER PUBLICATIONS

International Search Report & Written Opinion mailed Mar. 15, 2022, regarding PCT/CN2021/100698.

*Primary Examiner* — Chad A Newton
(74) *Attorney, Agent, or Firm* — Intellectual Valley Law, P.C.

(57) ABSTRACT

An intelligent healthcare management system is provided. The intelligent healthcare management system includes a distributed computing system including one or more networked computers configured to execute in parallel to perform at least one common task; and one or more computer readable storage mediums storing instructions that, when executed by the distributed computing system, cause the distributed computing system to execute software modules. The software modules includes an internet-of-things platform server; a business server; a physiological parameter data analysis platform configured to provide one or more user interfaces for point-of-care physiological parameter data collection; a business-end management platform configured to store and manage historical physiological parameter data of customers associated with a business entity; and a customer-end personal data management platform configured to manage personal historical physiological parameter data specific for an individual customer. The internet-of-things platform server and the business server are configured to exchange data between each other.

20 Claims, 18 Drawing Sheets

(58) Field of Classification Search
CPC ........ G16H 20/17; G16H 20/30; G16H 20/40;
G16H 20/60; G16H 20/70; G16H 20/90;
G16H 30/20; G16H 30/40; G16H 40/20;
G16H 40/40; G16H 40/60
See application file for complete search history.

(56) References Cited

U.S. PATENT DOCUMENTS

| | | | |
|---|---|---|---|
| 2008/0162352 A1 | 7/2008 | Gizewski | |
| 2017/0049383 A1* | 2/2017 | McMahon | A61B 5/14532 |
| 2019/0313246 A1* | 10/2019 | Nix | H04W 12/069 |
| 2020/0237291 A1* | 7/2020 | Sundaram | A61B 5/11 |
| 2021/0012869 A1* | 1/2021 | Kotlarz | G16H 15/00 |
| 2021/0019130 A1* | 1/2021 | Zou | G06F 8/60 |
| 2022/0157432 A1 | 5/2022 | Liu et al. | |

FOREIGN PATENT DOCUMENTS

| | | |
|---|---|---|
| CN | 103622684 A | 3/2014 |
| CN | 104523263 A | 4/2015 |
| CN | 106778017 A | 5/2017 |
| CN | 111383738 A | 7/2020 |
| CN | 111599428 A | 8/2020 |
| CN | 111667927 A | 9/2020 |
| CN | 211553735 U | 9/2020 |

* cited by examiner

| BOE | Intelligent healthcare management system | | | | | | |
|---|---|---|---|---|---|---|---|
| Customer Data Management | Customer Data Management | | | | | | |
| Customer Data Management | Name: ☐ Telephone Number ☐ [Search] [Reset] | | | | | | |
| Business Entity Management | | | | | | | |
| Authorization Management | Serial Number | Name | Sex | Phone Number | Birthday | Most recent results | Time taken | Action Item |
| | 1 | Customer 1 | Female | | | Fat: normal; Protein: normal; Glucose: low | 2021-02-05 | Detail Report |
| | 2 | Customer 2 | Female | | | Fat: normal; Protein: normal; Glucose: normal | 2021-01-20 | Detail Report |
| | 3 | Customer 3 | Female | | | Fat: normal; Protein: high; Glucose: low | 2021-01-20 | Detail Report |
| | 4 | Customer 4 | Female | | | Fat: normal; Protein: high; Glucose: low | 2021-01-20 | Detail Report |
| | 5 | Customer 5 | Female | | | Fat: high; Protein: low; Glucose: low | 2021-01-19 | Detail Report |
| | 6 | Customer 6 | Female | | | Fat: high; Protein: low; Glucose: low | 2021-01-19 | Detail Report |
| | 7 | Customer 7 | Female | | | Fat: high; Protein: low; Glucose: low | 2020-12-24 | Detail Report |
| | 8 | Customer 8 | Female | | | Fat: high; Protein: low; Glucose: low | 2020-12-24 | Detail Report |
| | 9 | Customer 9 | Female | | | Fat: high; Protein: high; Glucose: low | 2020-12-14 | Detail Report |

FIG. 7A

| BOE | Intelligent healthcare management system | | | | | | | |
|---|---|---|---|---|---|---|---|---|
| Customer Data Management | Customer Data Management | | | | | | | |
| Customer Data Management | Basic Customer Information | | | | | | | |
| Business Entity Management | Name: Customer 1　　Sex: Female　　　　　　　　　Birthday<br>Phone Number:　　　Identification Number:<br>Height: 180 cm　　　Weight: 60 kg　　　　　　　　Waist circumference | | | | | | | |
| Authorization Management | Trend: | | | | | | | |
| | Serial Number | Time taken | Stage of Milk | Fat (g/100g) | Protein (g/100g) | Glucose (g/100g) | Calory (kcal/100g) | Zinc (μg/ml) | Calcium (μg/ml) | Action Item |
| | 1 | 2021-01-20 | Mature | 5.13 | 1.16 | 4.96 | 70.6 | 6.5 | 378.73 | Detail Report |
| | 2 | 2021-01-20 | Mature | 7.52 | 1.01 | 4.47 | 89.46 | 6.5 | 370.14 | Detail Report |
| | 3 | 2021-01-20 | Mature | 7.52 | 1.01 | 4.47 | 89.46 | 6.5 | 370.14 | Detail Report |
| | 4 | 2021-01-20 | Mature | 7.8 | 0.9 | 4.78 | 92.78 | 6 | 340.56 | Detail Report |
| | 5 | 2021-01-19 | Mature | 7.14 | 1.31 | 4.42 | 87.08 | 4.66 | 400 | Detail Report |
| | 6 | 2021-01-19 | Mature | 7.14 | 1.31 | 4.42 | 87.08 | 4.66 | 400 | Detail Report |
| | 7 | 2021-01-19 | Mature | 7.14 | 1.31 | 4.42 | 87.08 | 4.66 | 400 | Detail Report |

FIG. 7B

Breast Milk physiological parameter report

Name: Customer 1　　Phone Number:　　　　Height: 160 cm　　Weight: 60 kg
Sex of baby: Male　　Birthday of baby: 2021-01-13　　Comments:

| Contents | Reference range | Unit | Results | Test date: 2021-01-20 |
|---|---|---|---|---|
| Fat | 1.80-5.50 | g/100g | 5.13 | |
| Protein | 0.75-1.30 | g/100g | 1.16 | |
| Glucose | 6.10-7.90 | g/100g | 4.96 ↓ | |
| Calory | 44.50-89.50 | kcal/100g | 70.6 | |
| Zinc | 1-5.2 | µg/ml | 6.5 ↑ | |
| Calcium | 180-330 | µg/ml | 378.73 ↑ | |

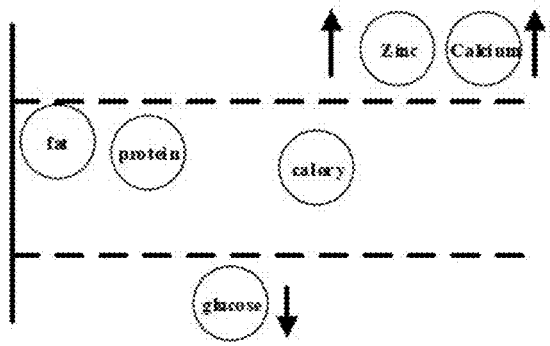

Analysis Results:
Fat content: normal level: The milk has normal content of this indicator. Good nutritional status.
Protein content: normal level: The milk has normal content of this indicator. Good nutritional status.
Glucose content: low: Glucose level is low. Inadequate lactose content in breast milk can lead to slow growth and affect the development of the brain's nervous system in the baby.
Calory: normal level: The milk has normal content of this indicator. Good nutritional status.
Zinc content: high: Too much zinc in the milk could affect metabolism of copper and iron in the baby, may lead to copper deficiency syndrome or iron deficiency anemia.
Calcium content: high: Too much calcium places a burden on the digestive system of the baby. Too much calcium in the long run increase the chance of stones in the urinary system, brittle bones prone to fracture, premature calcification of cartilage, etc.
Guidance:
Improper diet for nursing mom in the long term can lead to a decrease in quality of breast milk. Thus, it is important to ensure a balanced diet for nursing mom on a daily basis.
Medical / Nutritional Advice:

FIG. 7C

INTELLIGENT HEALTHCARE MANAGEMENT SYSTEM, INTELLIGENT HEALTHCARE MANAGEMENT METHOD, AND COMPUTER-PROGRAM PRODUCT

CROSS-REFERENCE TO RELATED APPLICATION

This application is a national stage application under 35 U.S.C. § 371 of International Application No. PCT/CN2021/100698, filed Jun. 17, 2021, the contents of which are incorporated by reference in the entirety.

TECHNICAL FIELD

The present invention relates to an intelligent healthcare management system, an intelligent healthcare management method, and a computer-program product.

BACKGROUND

Healthcare is provided by healthcare entities and healthcare facilities such as hospitals, laboratories, pharmacies, and others. To better provide healthcare to patients and customers, all healthcare entities are under increased pressure to improve their services without incurring additional costs. This demands the healthcare entities to become more efficient and effective in providing patient services to remain viable.

SUMMARY

In one aspect, the present disclosure provides an intelligent healthcare management system, comprising a distributed computing system comprising one or more networked computers configured to execute in parallel to perform at least one common task; and one or more computer readable storage mediums storing instructions that, when executed by the distributed computing system, cause the distributed computing system to execute software modules; wherein the software modules comprise an internet-of-things platform server; a business server; a physiological parameter data analysis platform configured to provide one or more user interfaces for point-of-care physiological parameter data collection; a business-end management platform configured to store and manage historical physiological parameter data of customers associated with a business entity; and a customer-end personal data management platform configured to manage personal historical physiological parameter data specific for an individual customer; wherein the internet-of-things platform server and the business server are configured to exchange data between each other; the internet-of-things platform server is configured to store and manage physiological parameter data measured by an internet-of-things physiological parameter data detector; and the business server is configured to be in interactive communication with the physiological parameter data analysis platform, the business-end management platform, and the customer-end personal data management platform, respectively.

Optionally, the physiological parameter data analysis platform is configured to cause a user terminal on which the physiological parameter data analysis platform is loaded to search for a nearby internet-of-things physiological parameter data detector available for pairing with the user terminal; cause to display a unique identification code of the internet-of-things physiological parameter data detector on the user terminal; provide a prompt signal on the user terminal requesting connection between the internet-of-things physiological parameter data detector and the user terminal; cause to display an authentication interface on the user terminal, operable to log a user into a user account; and cause to display a physiological parameter detection instructions on the user terminal.

Optionally, the physiological parameter data analysis platform is configured to cause to display a physiological parameter report listing one or more physiological parameters detected by the internet-of-things physiological parameter data detector on a user terminal on which the physiological parameter data analysis platform is loaded, and cause to display a two-dimensional bar code on the user terminal, operable to initiate a file transmission process, upon the two-dimensional bar code being scanned by a customer terminal, transmitting the physiological parameter report to the customer terminal.

Optionally, the physiological parameter data analysis platform is configured to cause to display a query interface, operable to query historical physiological parameter reports of customers associated with an entity.

Optionally, the physiological parameter data analysis platform is configured to cause to display an entity management interface, operable to perform at least one of inputting entity profile of an entity; querying upcoming customer reservation information; or video-conferencing with a customer.

Optionally, the intelligent healthcare management system further comprises the internet-of-things physiological parameter data detector, and the user terminal; wherein the user terminal is configured to search for the nearby internet-of-things physiological parameter data detector available for pairing; display the unique identification code of the internet-of-things physiological parameter data detector; display the prompt signal requesting connection with the internet-of-things physiological parameter data detector; upon receiving a response signal, establish the connection with the internet-of-things physiological parameter data detector; display the authentication interface, operable to log the user into a user account; and display the physiological parameter detection instructions.

Optionally, the business-end management platform is configured to cause to display a parameter query interface on a business-end terminal on which the business-end management platform is loaded, operable to query the historical physiological parameter data of customers associated with a business entity; and cause to display analysis results of historical physiological parameter data of customers associated with a business entity on the business-end terminal.

Optionally, the business-end management platform is configured to cause to display abnormality alert on the business-end terminal when the analysis results indicate one or more historical physiological parameter is abnormal.

Optionally, the internet-of-things platform server is further configured to analyze historical physiological parameter data of customers associated with a business entity, and generate analysis results; and the business server is configured to transmit the analysis results to the business-end management platform.

Optionally, the analysis results comprise data for visualization of the historical physiological parameter data; wherein the business server is configured to transmit the data for visualization of the historical physiological parameter data to the business-end management platform; and wherein the business-end management platform is configured to cause to display the data for visualization of the historical physiological parameter data for a respective customer, on a business-end terminal on which the business-end management platform is loaded.

Optionally, the business-end management platform is configured to cause to display an input interface, operable to input personalized medical or nutritional advice for a customer, on a business-end terminal on which the business-end management platform is loaded; wherein the business server is configured to sync the personalized medical or nutritional advice to the physiological parameter data analysis platform and the customer-end personal data management platform.

Optionally, the business-end management platform is configured to cause to display a customer query interface on a business-end terminal on which the business-end management platform is loaded, operable to query customer information of customers associated with a business entity.

Optionally, the business-end management platform is configured to cause to display a business query interface on a business-end terminal on which the business-end management platform is loaded, operable to query operation information of a business entity.

Optionally, the internet-of-things platform server is further configured to apply big data analysis on historical physiological parameter data stored on the internet-of-things platform server, and generate population classification data classifying the population into sub-populations respectively having similar physiological parameter profiles; wherein the business server is configured to transmit the population classification data to the customer-end personal data management platform; and wherein the customer-end personal data management platform is configured to cause to display a sub-population classification corresponding to the individual customer's physiological parameter profile on a customer terminal on which the customer-end personal data management platform is loaded.

Optionally, the internet-of-things platform server is further configured to generate medical or nutritional advice for a respective sub-population having a respective similar physiological parameter profile; wherein the business server is configured to transmit the medical or nutritional advice to the customer-end personal data management platform; and wherein the customer-end personal data management platform is configured to cause to display the medical or nutritional advice on the customer terminal.

Optionally, the customer-end personal data management platform is configured to cause to associate the individual customer's account with a community forum targeting a respective sub-population having a respective physiological parameter profile similar to the individual customer's physiological parameter profile, the community forum allowing the individual customer to interact with members of the community forum.

Optionally, the customer-end personal data management platform is configured to cause to display medical or nutritional knowledge data on a customer terminal on which the customer-end personal data management platform is loaded.

Optionally, the customer-end personal data management platform is configured to cause to display a reservation interface, operable to reserve an appointment for the point-of-care physiological parameter data collection; and/or cause to display a ranking interface, operable to allow the individual customer to rank service provided by the business entity hosting the point-of-care physiological parameter data collection.

Optionally, the customer-end personal data management platform is configured to allow the individual customer's account to access an online shop for purchasing merchandise.

Optionally, the point-of-care physiological parameter data collection comprises breast milk content data collection; and the internet-of-things physiological parameter data detector is a breast milk analyzer.

In another aspect, the present disclosure provides an intelligent healthcare management method performed by a distributed computing system comprising one or more networked computers configured to execute in parallel to perform at least one common task; the method comprising executing an internet-of-things platform server; executing a business server; executing a physiological parameter data analysis platform configured to provide one or more user interfaces for point-of-care physiological parameter data collection; executing a business-end management platform configured to store and manage historical physiological parameter data of customers associated with a business entity; and executing a customer-end personal data management platform configured to manage personal historical physiological parameter data specific for an individual customer; wherein the internet-of-things platform server and the business server are configured to exchange data between each other; the internet-of-things platform server is configured to store and manage physiological parameter data measured by an internet-of-things physiological parameter data detector; and the business server is configured to be in interactive communication with the physiological parameter data analysis platform, the business-end management platform, and the customer-end personal data management platform, respectively.

In another aspect, the present disclosure provides a computer-program product, for intelligent healthcare management, comprising a non-transitory tangible computer-readable medium having computer-readable instructions thereon, the computer-readable instructions being executable by a processor, in a distributed computing system comprising one or more networked computers configured to execute in parallel to perform at least one common task, to cause the processor to perform executing an internet-of-things platform server; executing a business server; executing a physiological parameter data analysis platform configured to provide one or more user interfaces for point-of-care physiological parameter data collection; executing a business-end management platform configured to store and manage historical physiological parameter data of customers associated with a business entity; and executing a customer-end personal data management platform configured to manage personal historical physiological parameter data specific for an individual customer; wherein the internet-of-things platform server and the business server are configured to exchange data between each other; the internet-of-things platform server is configured to store and manage physiological parameter data measured by an internet-of-things physiological parameter data detector; and the business server is configured to be in interactive communication with the physiological parameter data analysis platform, the business-end management platform, and the customer-end personal data management platform, respectively.

BRIEF DESCRIPTION OF THE FIGURES

The following drawings are merely examples for illustrative purposes according to various disclosed embodiments and are not intended to limit the scope of the present invention.

FIG. 7A to FIG. 7C illustrate operation of a business-end management platform in detecting breast milk nutritional contents.

DETAILED DESCRIPTION

The disclosure will now be described more specifically with reference to the following embodiments. It is to be noted that the following descriptions of some embodiments are presented herein for purpose of illustration and description only. It is not intended to be exhaustive or to be limited to the precise form disclosed.

The present disclosure provides, inter alia, an intelligent healthcare management system, an intelligent healthcare management method, and a computer-program product that substantially obviate one or more of the problems due to limitations and disadvantages of the related art. In one aspect, the present disclosure provides an intelligent healthcare management system. In some embodiments, the intelligent healthcare management system includes a distributed computing system comprising one or more networked computers configured to execute in parallel to perform at least one common task; and one or more computer readable storage mediums storing instructions that, when executed by the distributed computing system, cause the distributed computing system to execute software modules. Optionally, the software modules include an internet-of-things platform server; a business server; a physiological parameter data analysis platform configured to provide one or more user interfaces for point-of-care physiological parameter data collection; a business-end management platform configured to store and manage historical physiological parameter data of customers associated with a business entity; and a customer-end personal data management platform configured to manage personal historical physiological parameter data specific for an individual customer. Optionally, the internet-of-things platform server and the business server are configured to exchange data between each other; the internet-of-things platform server is configured to store and manage physiological parameter data measured by an internet-of-things physiological parameter data detector; and the business server is configured to be in interactive communication with the physiological parameter data analysis platform, the business-end management platform, and the customer-end personal data management platform, respectively.

Figure 1:
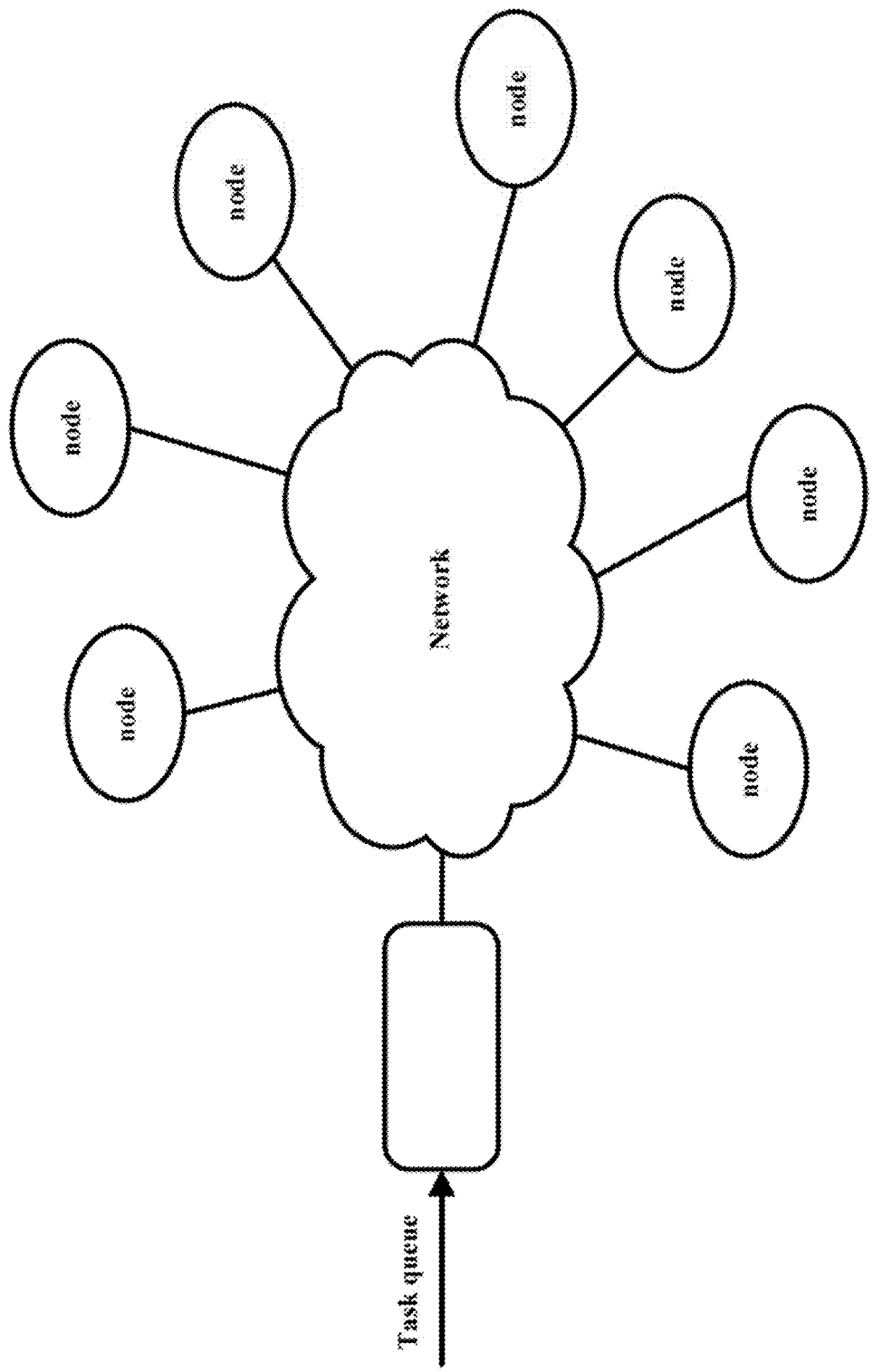
FIG. 1 illustrates a distributed computing environment in some embodiments according to the present disclosure.

FIG. 1 illustrates a distributed computing environment in some embodiments according to the present disclosure. Referring to FIG. 1, in a distributed computing environment, a number of autonomous computers/workstations, called nodes, are in communication with one another in a network, for example, a LAN (Local Area Network), to solve a task, such as execute an application. Each of the computer nodes typically includes its own processor(s), memory and a communication link to other nodes. The computers can be located within a particular location (e.g. cluster network) or can be connected over a large area network such as the Internet. In such a distributed computing environment, different applications may share information and resources.

Multiple computing nodes are configured to join a resource group in order to provide distributed services. A computing node in the distributed network may include any type of computing devices such as a user device. A computing node may also include data centers. As used herein, a computing node may refer to any computing device or multiple computing device (i.e., a data center). Software modules may be executed on a single computing node (e.g., a server) or distributed across multiple nodes in any suitable manner.

The distributed computing environment may also include one or more storage nodes for storing information related to execution of software modules, and/or output generated by execution of software modules, and/or other functions. The one or more storage nodes are in communication with one another in a network, and are in communication with one or more of the computing nodes in the network.

The distributed computing system includes one or more networked computers configured to execute in parallel to perform at least one common task, for example, manage, process, and/or analyze data collected from a plurality of devices such as internet-of-things devices.

In some embodiments, the network in the distributed computing environment may include an internet-of-things network. The term "internet-of-things" may refer to uniquely identifiable objects (things) and their virtual representations in a network-based architecture. In particular, the internet-of-things involves the ability to connect more than just computers and communications devices, but rather the ability to connect "objects" in general, such as lights, appliances, vehicles, heating, ventilating, and air-conditioning (HVAC), windows and window shades and blinds, doors, locks, etc.

Figure 2A:
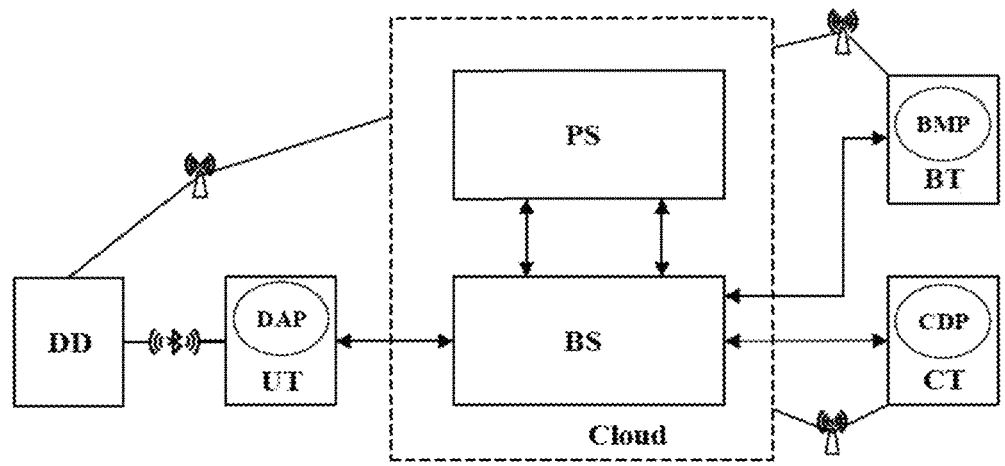
FIG. 2A illustrates software modules in an intelligent healthcare management system in some embodiments according to the present disclosure.

FIG. 2A illustrates software modules in an intelligent healthcare management system in some embodiments according to the present disclosure. Referring to FIG. 2A, the intelligent healthcare management system in some embodiments includes an internet-of-things platform server PS and a business server BS, e.g., in the cloud. In one example, the cloud is a public cloud. In another example, the cloud is a private cloud. In another example, the cloud is a hybrid cloud. A public cloud is a cloud computing system that provides subscription of cloud services to the general public. Examples of public cloud include Microsoft Azure®, Amazon Web Services®, and Google Compute®. A private cloud is a cloud computing system for internal use of and under strict access control of an organization due to security, data protection, privacy, or other concerns. A public cloud or users outside of an organization typically do not have access to a private cloud of the organization. A hybrid cloud is a cloud computing system having a portion being a public cloud interconnected to another portion that is a private cloud.

The internet-of-things platform server PS may be a server that obtains, stores, and manages internet-of-things device information about each of a plurality of devices (e.g., including internet-of-things devices, mobile phones, etc.). The internet-of-things platform server PS may obtain, determine, or generate a control command for controlling the device (e.g., an internet-of-things device) by using the stored device information. In one example, the internet-of-things platform server PS is configured to store and manage physiological parameter data measured by an internet-of-things physiological parameter data detector.

In some embodiments, the intelligent healthcare management system further includes a physiological parameter data analysis platform DAP configured to provide one or more user interfaces for point-of-care physiological parameter data collection. In one example, the physiological parameter data analysis platform DAP is loaded on a user terminal UT. In another example, the physiological parameter data analysis platform DAP is a mobile application installed on the user terminal UT. In another example, the intelligent healthcare management system further includes the user terminal UT. The ter "point-of-care" as used herein can be defined to mean a location on or near a site of patient care where medical or medically related services such as medical testing and/or treatment can be provided, including but not limited to hospitals, emergency departments, intensive care units, primary care setting, medical centers, patient homes, a physician's office, a pharmacy or a site of an emergency.

Various appropriate physiological parameter data may be detected by the present intelligent healthcare management system. Examples of suitable physiological parameter data include blood pressure, blood glucose level, body fat level, pulse rate, body temperature, electrocardiography parameters, electroencephalography parameters, levels of various markers in various biological samples (e.g., blood, break milk, mucus, urine, tumor tissue, stool, saliva, biopsy sample, gastrointestinal tissue).

In some embodiments, the intelligent healthcare management system further includes an internet-of-things physiological parameter data detector DD. In one example, the internet-of-things physiological parameter data detector DD is configured to be connected to the user terminal UT, e.g., through a Bluetooth connection. In another example, the internet-of-things physiological parameter data detector DD is configured to be connected to the cloud through the user terminal UT. In another example, the internet-of-things physiological parameter data detector DD is configured to be connected to the cloud independently through, e.g., a WAN or a LAN. In one example, the internet-of-things physiological parameter data detector DD is situated in a business entity, and a customer may come into the business entity to have the physiological parameter data collected in the business entity. In another example, the internet-of-things physiological parameter data detector DD is situated in a customer's home, and the customer may conveniently have the physiological parameter data collected at home.

Figure 2B:
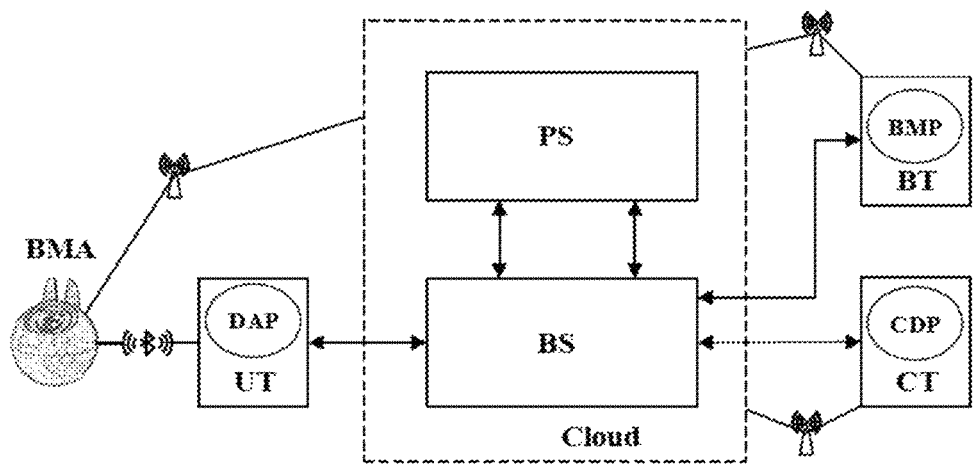
FIG. 2B illustrates software modules in an intelligent healthcare management system in some embodiments according to the present disclosure.

FIG. 2B illustrates software modules in an intelligent healthcare management system in some embodiments according to the present disclosure. Referring to FIG. 2B, in some embodiments, the internet-of-things physiological parameter data detector is a breast milk analyzer BMA. In one example, the breast milk analyzer BMA is configured to detect nutritional contents of the breast milk, e.g., contents/levels of protein, lipid/fat, calcium, zinc, glucose, and calories in the breast milk.

Referring to FIG. 2A and FIG. 2B, the intelligent healthcare management system in some embodiments further includes a business-end management platform BMP. In one example, the business-end management platform BMP is loaded on a business terminal BT. In another example, the intelligent healthcare management system further includes the business terminal BT. The business terminal BT is configured to be connected to the cloud through, e.g., a WAN or a LAN. In some embodiments, the business-end management platform BMP is configured to store and manage historical physiological parameter data of customers associated with a business entity. In one example, the business-end management platform BMP is a software-as-a-service (SaaS) platform. The term "SaaS" is the abbreviation of "software as a service". For example, the term "SaaS" means a cloud service providing model including a function that allows a company or individual (user) who does not possess a data center (cloud server) to use, via a network such as the Internet, an application provided by a platform provider who possesses a data center (cloud server).

In some embodiments, the intelligent healthcare management system further includes a customer-end personal data management platform CDP. In one example, the customer-end personal data management platform CDP is loaded on a customer terminal CT. In another example, the customer terminal CT and the user terminal UT may be a same terminal, for example, the physiological parameter data analysis platform DAP and the customer-end personal data management platform CDP are both loaded on a same terminal (e.g., a smart phone). In another example, the intelligent healthcare management system further includes the customer terminal CT. The customer terminal CT is configured to be connected to the cloud through, e.g., a WAN or a LAN. In some embodiments, the customer-end personal data management platform CDP is configured to manage personal historical physiological parameter data specific for an individual customer.

In some embodiments, the customer-end personal data management platform CDP is an applet, e.g., an installation-free applet that does not require to be installed (does not require any installation processes to be executed on the customer terminal CT). In some embodiments, after downloading a program package of the customer-end personal data management platform CDP, the customer terminal CT can directly run the program package. In some embodiments, the applet is loaded on another application. For example, the customer may tap or touch on an icon of the installation-free applet in the another application (e.g., a social media application); the customer terminal CT loads a program package of the installation-free applet, and executes the program package. After the installation-free applet is disabled, the customer terminal CT automatically releases a resource occupied by the installation-free applet, in order to avoid occupying space of the customer terminal CT for an extended time period. In some embodiments, the applet is an installation-free and download-free application. For example, a user may simply scan a quick-response bar code of the applet, or search for the applet through a social media application to load a corresponding applet page in the social media application.

In some embodiments, the internet-of-things platform server PS and the business server BS are configured to exchange data between each other. In some embodiments, the internet-of-things platform server PS is configured to store and manage physiological parameter data measured by an internet-of-things physiological parameter data detector DD. In some embodiments, the business server BS is configured to be in interactive communication with the physiological parameter data analysis platform DAP, the business-end management platform BMP, and the customer-end personal data management platform CDP, respectively. For example, the physiological parameter data detected by the physiological parameter data analysis platform DAP is transmitted to the business server BS, which in turn transmit the physiological parameter data to the internet-of-things platform server PS.

Figure 3:
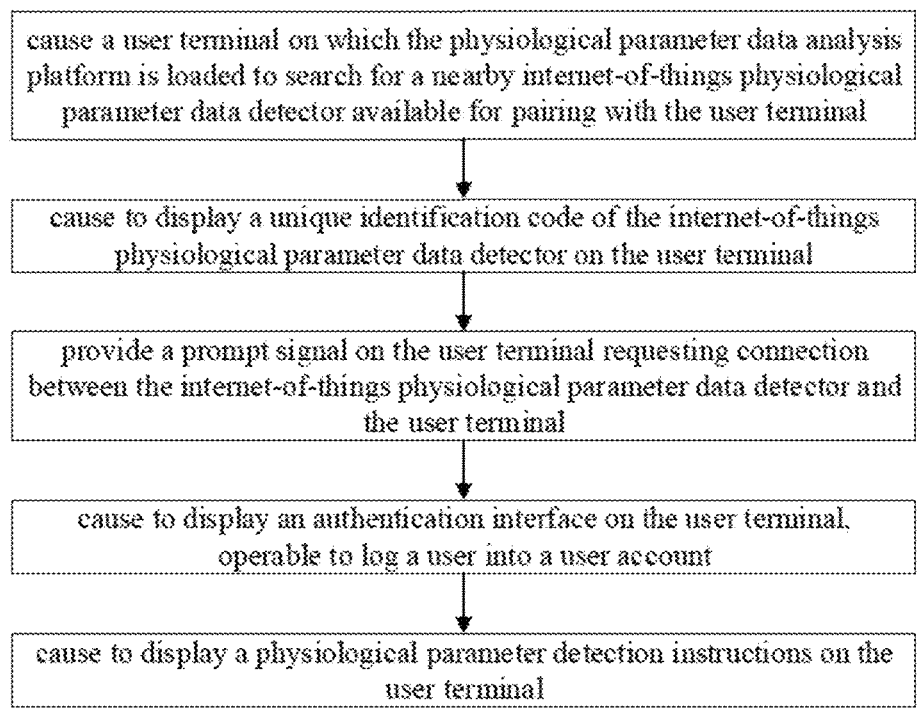
FIG. 3 illustrates a physiological parameter data analysis platform in some embodiments according to the present disclosure.

FIG. 3 illustrates a physiological parameter data analysis platform in some embodiments according to the present disclosure. Referring to FIG. 3, the physiological parameter data analysis platform in some embodiments is configured to cause a user terminal on which the physiological parameter data analysis platform is loaded to search for a nearby internet-of-things physiological parameter data detector available for pairing with the user terminal; cause to display a unique identification code of the internet-of-things physiological parameter data detector on the user terminal; provide a prompt signal on the user terminal requesting connection between the internet-of-things physiological parameter data detector and the user terminal; cause to display an authentication interface on the user terminal, operable to log a user into a user account; and cause to display a physiological parameter detection instructions on the user terminal.

In some embodiments, the intelligent healthcare management system further includes an internet-of-things physiological parameter data detector. In some embodiments, the intelligent healthcare management system further includes a user terminal. Optionally, the user terminal is a mobile phone. Optionally, the user terminal is a handheld device. In some embodiments, the user terminal is configured to search for the nearby internet-of-things physiological parameter data detector available for pairing; display the unique identification code of the internet-of-things physiological parameter data detector; display the prompt signal requesting connection with the internet-of-things physiological parameter data detector; upon receiving a response signal, establish the connection with the internet-of-things physiological parameter data detector; display the authentication interface, operable to log the user into a user account; and display the physiological parameter detection instructions.

FIG. 4A to FIG. 4H illustrate a physiological parameter data analysis platform in detecting breast milk nutritional contents. As an illustrative example, FIG. 4A to FIG. 4H describe a physiological parameter data analysis platform for detecting and analyzing breast milk contents. However, the physiological parameter data analysis platform according to the present disclosure is not limited to a breast milk analyzer, and may be implemented for detecting physiological parameter for any suitable samples or tissues.

Figure 4A:
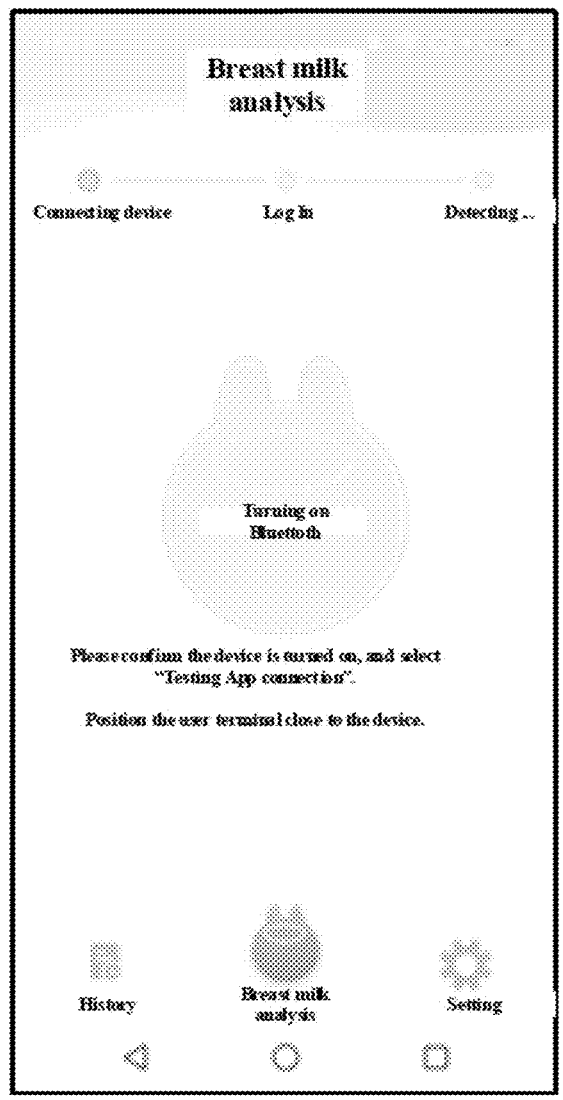
FIG. 4A to FIG. 4H illustrate operation of a physiological parameter data analysis platform in detecting breast milk nutritional contents.

Referring to FIG. 4A, the physiological parameter data analysis platform cause to display a user interface ("Breast milk analysis" interface). Upon activating a virtual object "Breast milk analysis" on the bottom of the interface, the physiological parameter data analysis platform cause to a user terminal on which the physiological parameter data analysis platform is loaded to search for a nearby internet-of-things physiological parameter data detector available for pairing with the user terminal (see, e.g., FIG. 4A, "Turning on Bluetooth" message). The breast milk analyzer is turned on, and a user may click on "Testing App connection" on the breast milk analyzer.

Figure 4B:
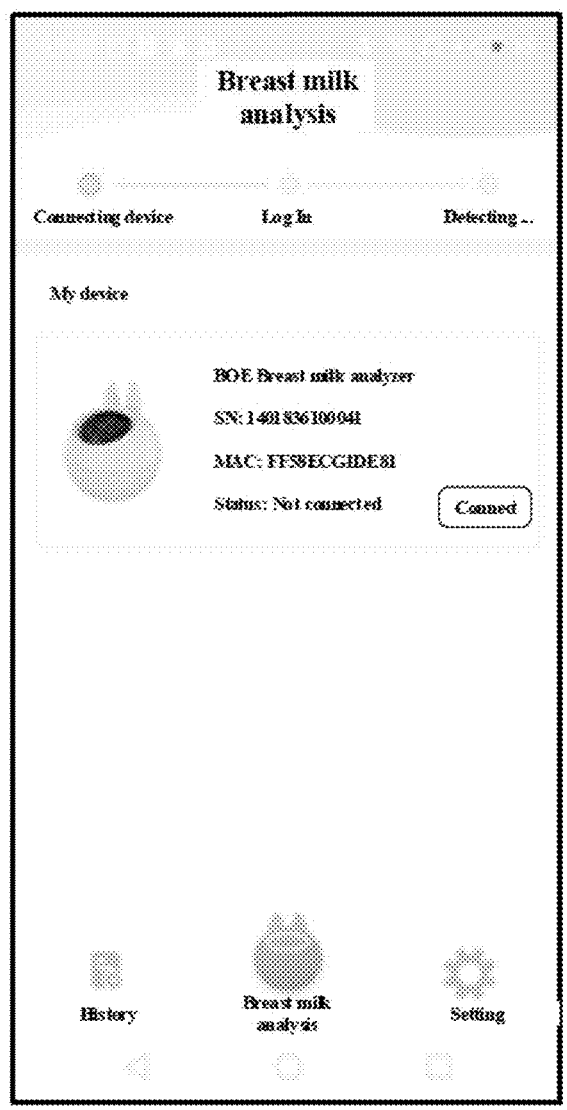
Figure 4C:
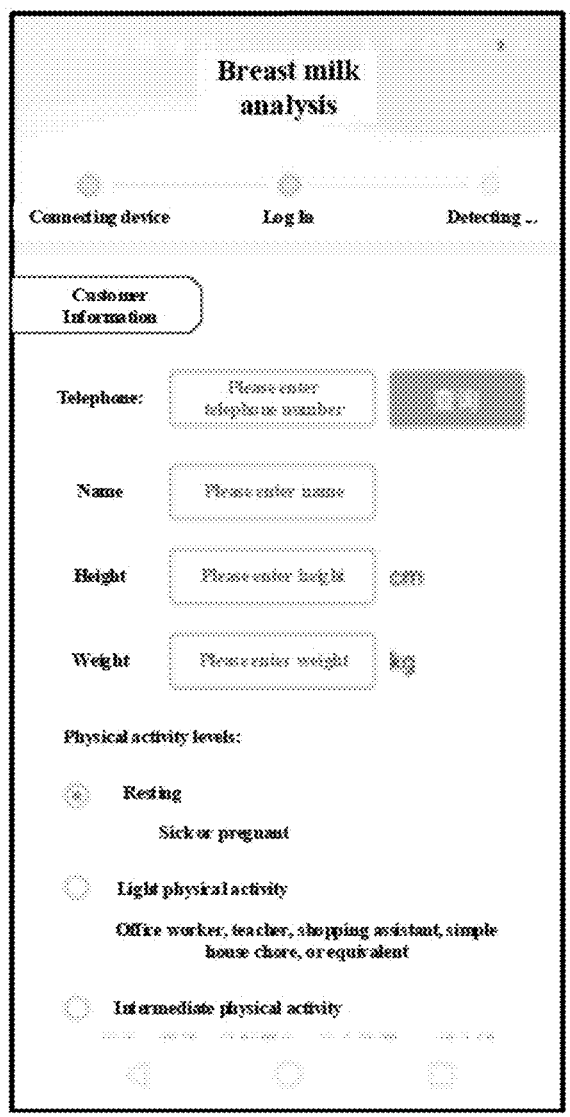

Referring to FIG. 4B, the user terminal searches for the nearby internet-of-things physiological parameter data detector available for pairing. When a breast milk analyzer is found, the physiological parameter data analysis platform causes to display a unique identification code (e.g., "SN: 140183610041" in FIG. 4B) of the internet-of-things physiological parameter data detector on the user terminal. The physiological parameter data analysis platform is configured to provide a prompt signal (e.g., the "Connect" virtual object in FIG. 4B) on the user terminal requesting connection between the internet-of-things physiological parameter data detector and the user terminal Referring to FIG. 4C, the physiological parameter data analysis platform causes to display an authentication interface on the user terminal, operable to log a user into a user account. FIG. 4C shows the authentication interface for a new customer that has not set up an account. The authentication interface requests the new customer to enter customer information such as telephone number, name, height, weight, and physical activity levels of the new customer. Once the account is set up, the customer may log in next time when they navigate to the authentication interface. Optionally, the physiological parameter data analysis platform enables facial recognition function to log in a customer into her account. The customer information entered into the physiological parameter data analysis platform may be used for generating personalized nutritional advice.

Figure 4D:
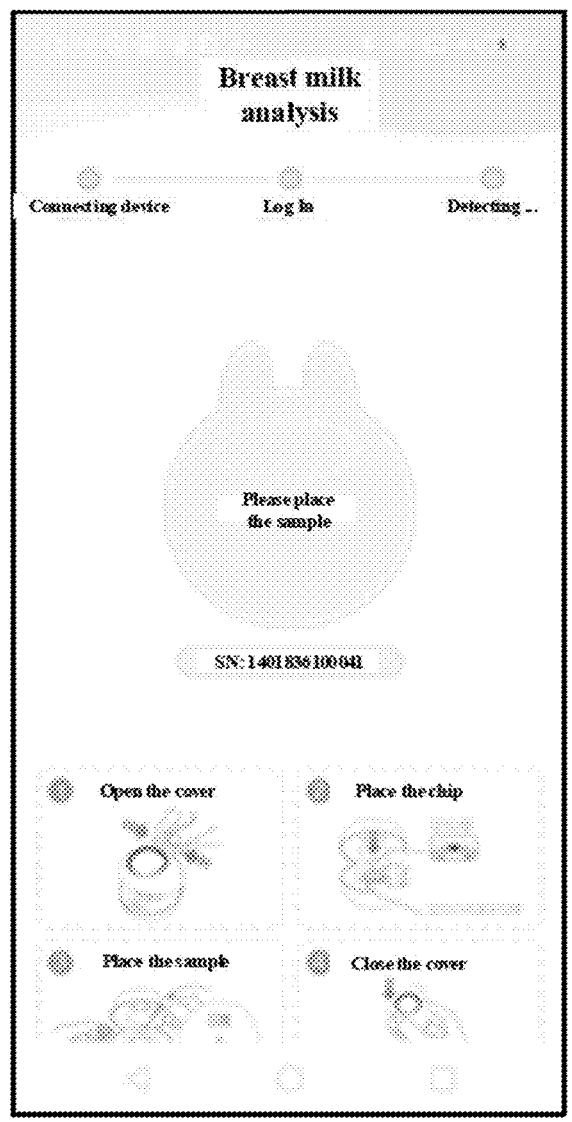
Figure 4E:
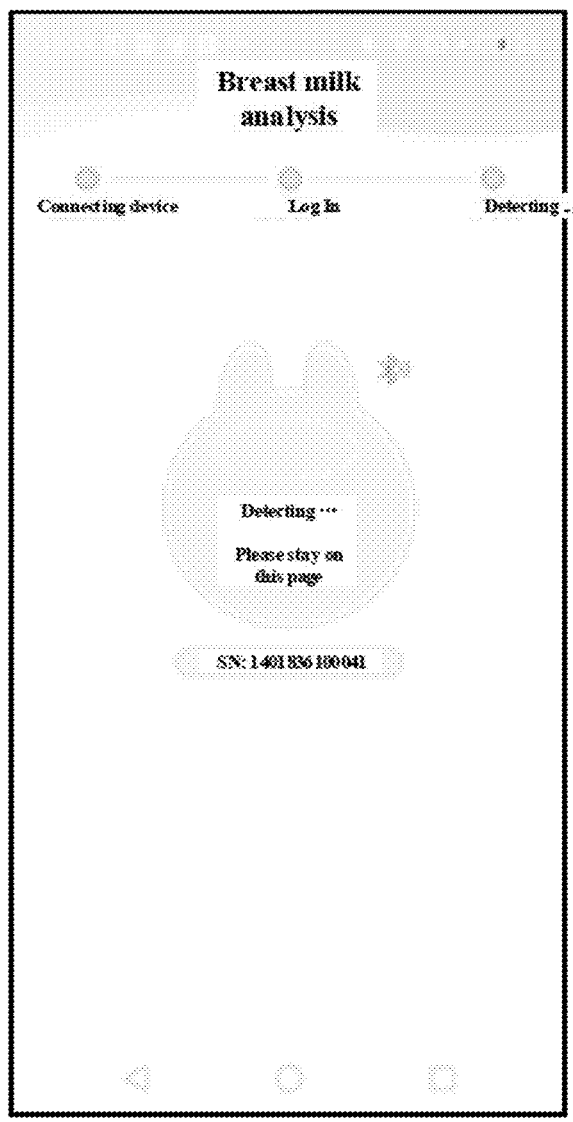

Referring to FIG. 4D, the physiological parameter data analysis platform causes to display a physiological parameter detection instructions on the user terminal. As shown in FIG. 4D, the instructions may include, for example, (1) open the cover of the breast milk analyzer; (2) place the chip into the breast milk analyzer; (3) place the breast milk sample into the breast milk analyzer; and (4) close the cover of the breast milk analyzer. Referring to FIG. 4E, the physiological parameter data analysis platform causes to display an instruction "Detecting . . . Please stay on this page".

Figure 4F:
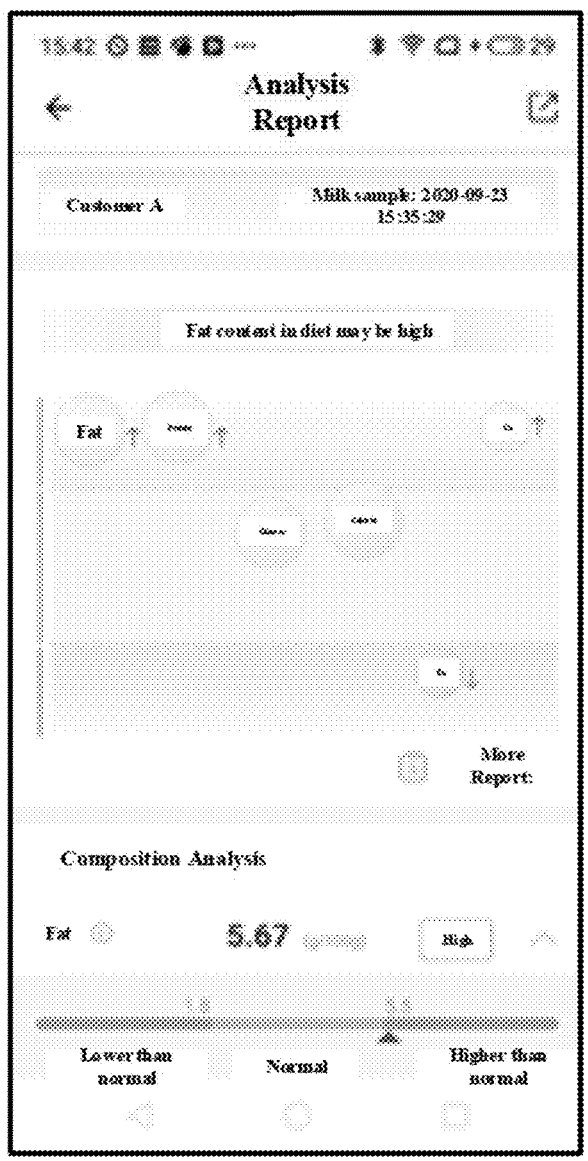

In some embodiments, the physiological parameter data analysis platform is further configured to cause to display a physiological parameter report listing one or more physiological parameters detected by the internet-of-things physiological parameter data detector on a user terminal on which the physiological parameter data analysis platform is loaded. Referring to FIG. 4F, the physiological parameter report ("Analysis Report" in FIG. 4F) lists contents of fat, protein, glucose, calcium, zinc, and calories. The physiological parameter report may be displayed in a graphical format. The physiological parameter report may provide personalized nutritional advice (e.g., "Fat content in diet may be high"). The physiological parameter report may further provide composition analysis of the sample.

Figure 4G:
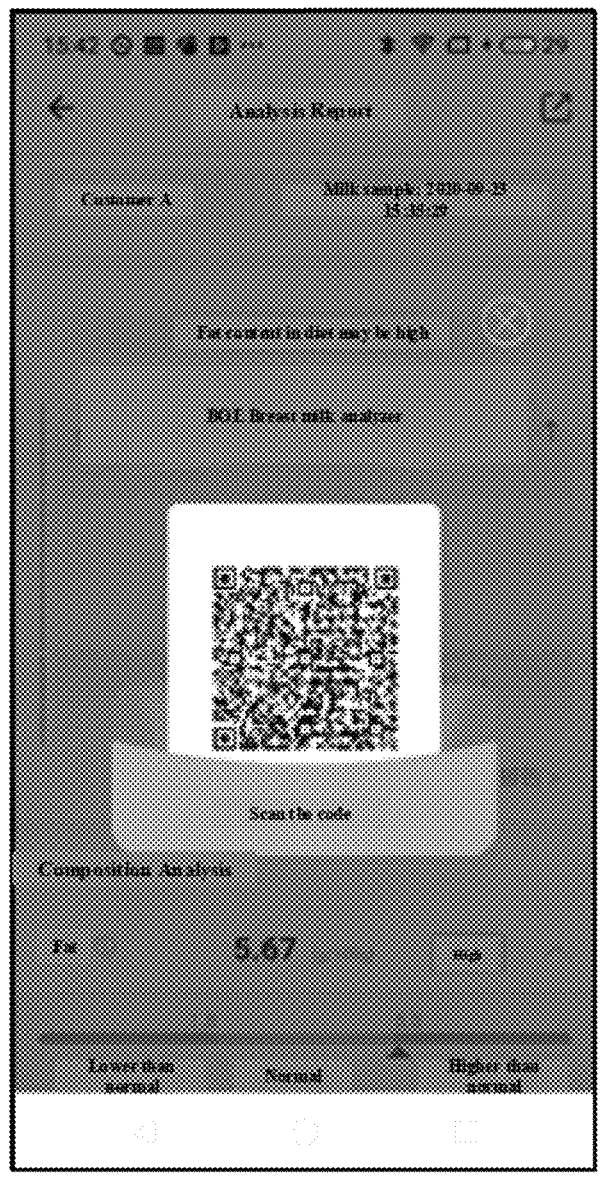

In some embodiments, the physiological parameter data analysis platform is further configured to cause to display a two-dimensional bar code on the user terminal, operable to initiate a file transmission process, upon the two-dimensional bar code being scanned by a customer terminal, transmitting the physiological parameter report to the customer terminal. Referring to FIG. 4G, the two-dimensional bar code may be a quick response bar code, which may be scanned by a customer A's mobile phone. Upon the quick response bar code being scanned by the customer A's mobile phone, the physiological parameter report is transmitted to the customer A's mobile phone.

Figure 4H:

In some embodiments, the physiological parameter data analysis platform is further configured to cause to display a query interface, operable to query historical physiological parameter reports of customers associated with an entity (e.g., reports generated at an entity hosting the internet-of-things physiological parameter data detector). Referring to FIG. 4H, the query interface is operable to query by customer's name or contact information. Moreover, the customer may search for "All" historical report, "Normal reports", reports "To be recorded", and reports generated while having an "Abnormal chip" placed in the breast milk analyzer. The customer may search reports dated between an "Earliest time" and "End time".

In some embodiments, the physiological parameter data analysis platform is further configured to cause to display an entity management interface, operable to perform at least one of: inputting entity profile of an entity (e.g., an entity hosting the internet-of-things physiological parameter data detector); querying upcoming customer reservation information; or video-conferencing with a customer. For example, when the physiological parameter data analysis platform is associated with a business entity, an employee of the business entity may log into the business entity's account, and may set up entity profile of the entity to promote the business of the entity. The employee of the business entity may also prepare the equipment and arrange required personnel (e.g., doctor, nurse, nutritionist) in view of upcoming customer reservation. The video-conferencing is particularly useful when the customer is preparing the physiological parameter data collection at home (e.g., the internet-of-things physiological parameter data detector DD is situated in a customer's home).

Figure 5A:
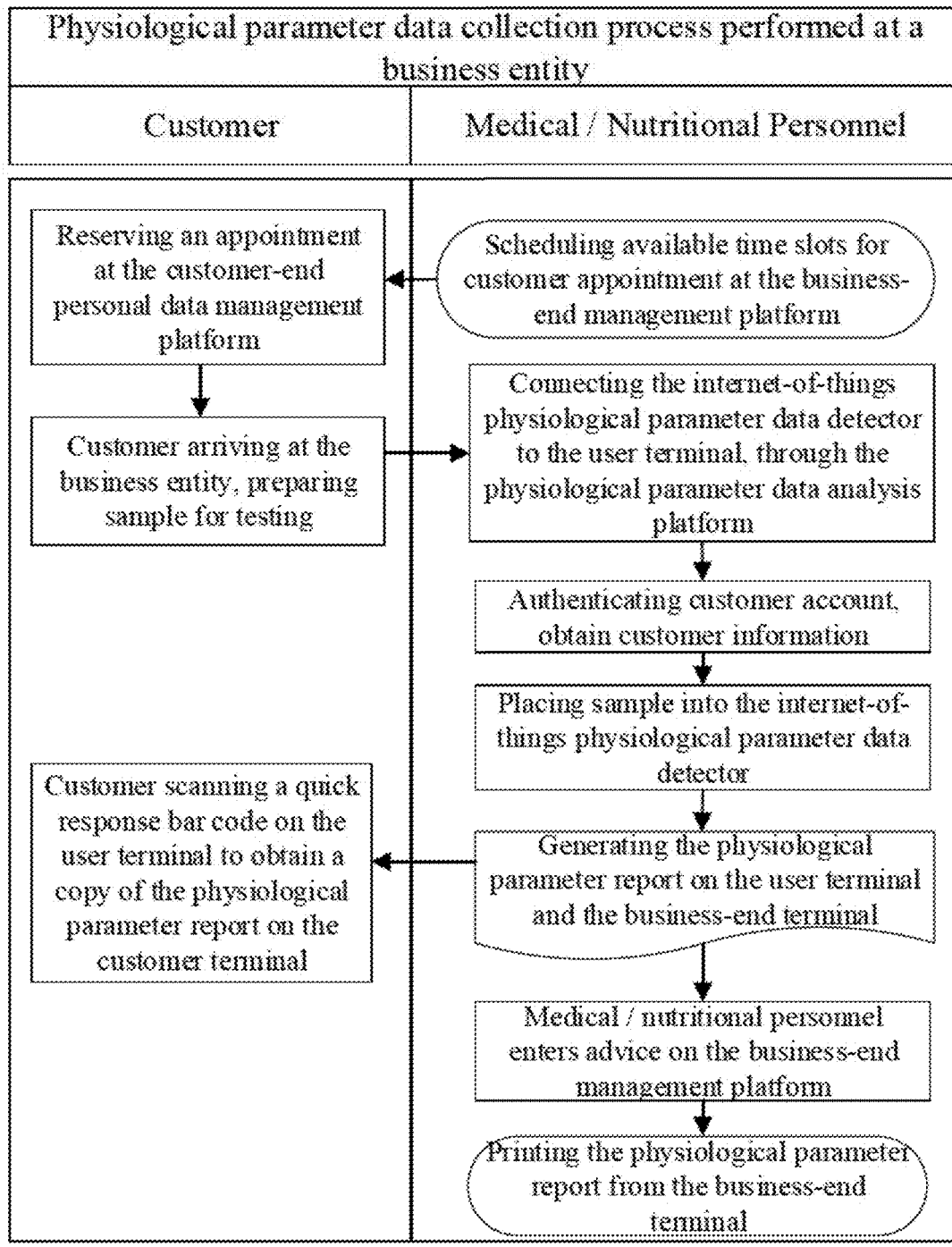
FIG. 5A illustrates a point-of-care physiological parameter data collection process in some embodiments according to the present disclosure.

As discussed previously, the physiological parameter data collection may be performed either at a business entity or at a customer's home. FIG. 5A illustrates a point-of-care physiological parameter data collection process in some embodiments according to the present disclosure. FIG. 5A illustrates a point-of-care physiological parameter data collection process performed at a business entity associated with the customer. The internet-of-things physiological parameter data detector is situated in a business entity, and a customer may come into the business entity to have the physiological parameter data collected in the business entity. Referring to FIG. 5A, at the business entity side, the medical/nutritional personnel schedules available time slots for customer appointment at the business-end management platform. At the customer side, the customer reserves an appointment at the customer-end personal data management platform. At the time of the appointment, the customer goes to the business entity, and prepares sample (e.g., breast milk sample) for testing. At the business entity side, when the customer arrives, the medical/nutritional personnel connects the internet-of-things physiological parameter data detector to the user terminal, through the physiological parameter data analysis platform. The physiological parameter data analysis platform authenticates the customer account, and obtains customer information. The medical/nutritional personnel (or the customer) places the milk sample into the internet-of-things physiological parameter data detector. When the detection is complete, the physiological parameter report is generated on the user terminal and the business-end terminal. The medical/nutritional personnel can enter medical/nutritional advice on the business-end management platform. The physiological parameter report may be printed from the business-end terminal.

Figure 5B:
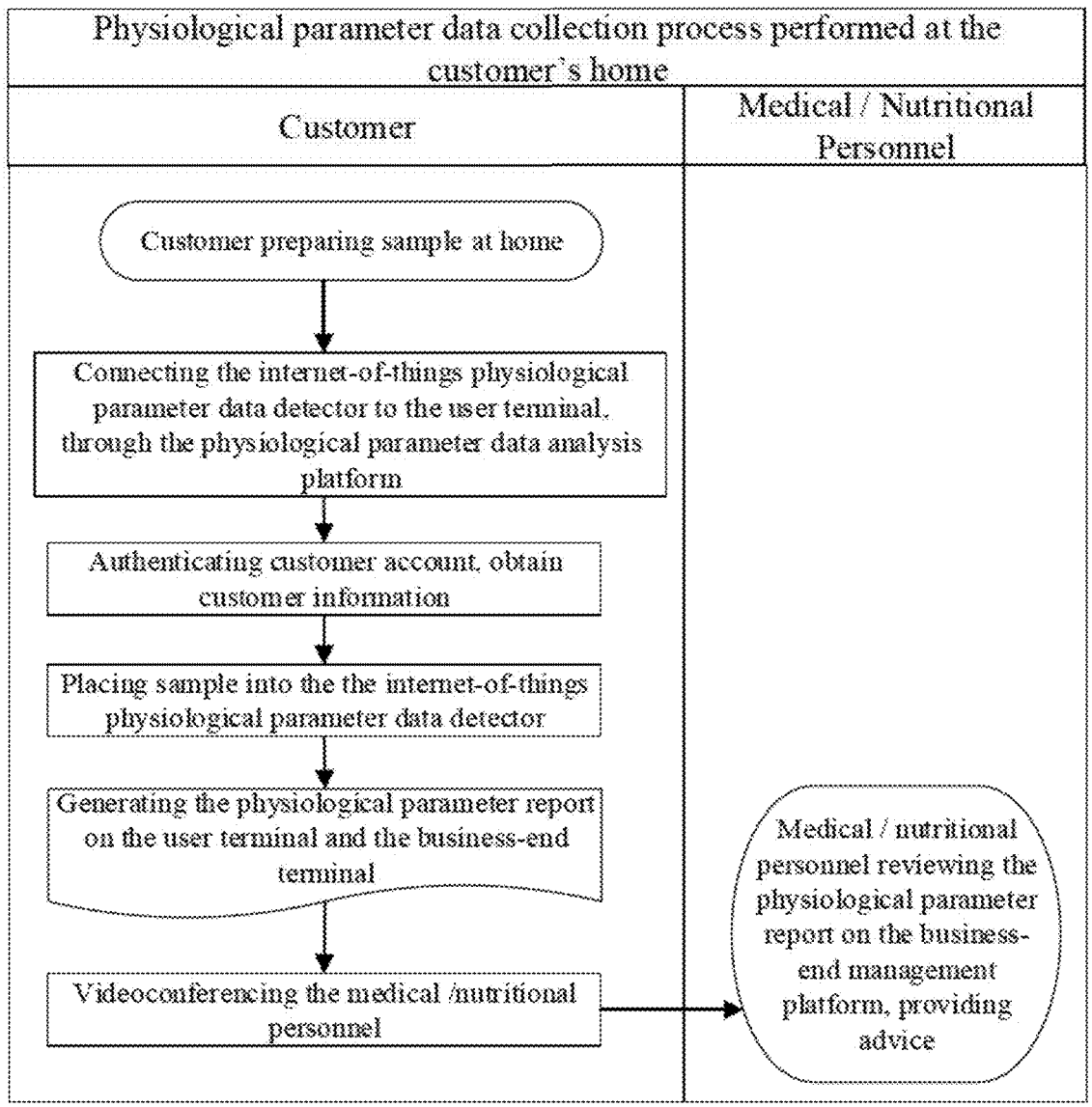
FIG. 5B illustrates a point-of-care physiological parameter data collection process in some embodiments according to the present disclosure.

FIG. 5B illustrates a point-of-care physiological parameter data collection process in some embodiments according to the present disclosure. FIG. 5B illustrates a point-of-care physiological parameter data collection process performed at the customer's home. The internet-of-things physiological parameter data detector is situated in a customer's home, and the customer may conveniently have the physiological parameter data collected at home. Referring to FIG. 5B, the customer prepares sample (e.g., milk sample) at her own home. The physiological parameter data analysis platform connects the internet-of-things physiological parameter data detector to the user terminal (in this case, can be the customer's mobile phone). The physiological parameter data analysis platform authenticates the customer account, and obtains customer information. The customer places the milk sample into the internet-of-things physiological parameter data detector. When the detection is complete, the physiological parameter report is generated on the user terminal and the business-end terminal. The customer may video-conference with the medical 1 nutritional personnel. At the business entity side, the medical/nutritional personnel may review the physiological parameter report. During the video conference, the medical/nutritional personnel can advise the customer on how to improve her condition (e.g., nutritional advice on how to improve milk nutritional contents). The medical/nutritional personnel may also enter medical/nutritional advice on the business-end management platform.

Figure 6:
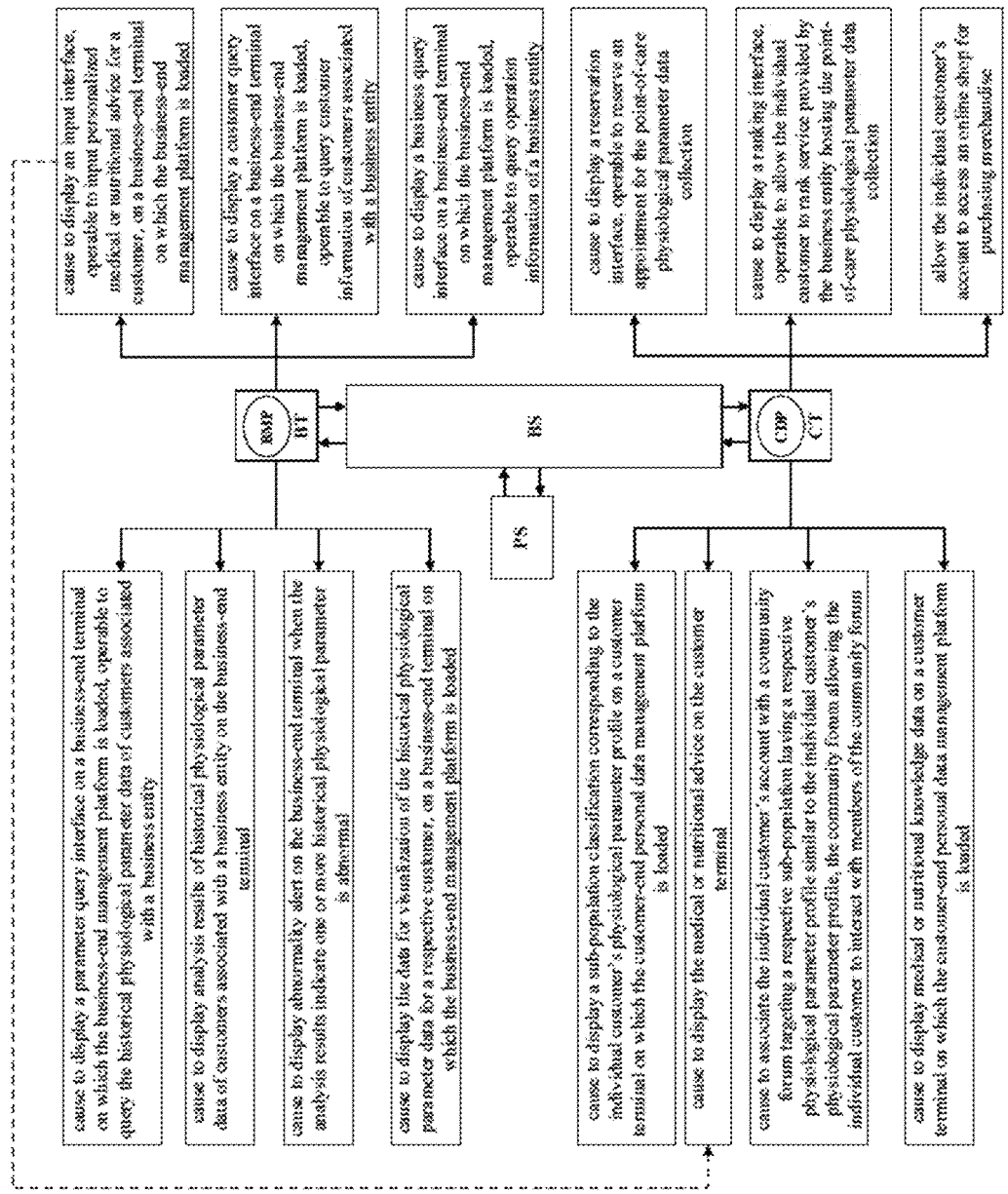
FIG. 6 illustrates a business-end management platform, a customer-end personal data management platform, an internet-of-things platform server, and a business server in some embodiments according to the present disclosure.

FIG. 6 illustrates a business-end management platform, a customer-end personal data management platform, an internet-of-things platform server, and a business server in some embodiments according to the present disclosure. Referring to FIG. 6, the business-end management platform in some embodiments is configured to cause to display a parameter query interface on a business-end terminal on which the business-end management platform is loaded, operable to query the historical physiological parameter data of customers associated with a business entity. FIG. 7A to FIG. 7C illustrate operation of a business-end management platform in detecting breast milk nutritional contents. FIG. 7A shows a parameter query interface displayed on the business-end terminal on which the business-end management platform BMP is loaded. The parameter query interface may be utilized to query the historical physiological parameter data of customers associated with a business entity. The historical physiological parameter data of customers associated with the business entity may be queried based on name, contact information, etc.

As shown in FIG. 7A, the business-end management platform BMP in some embodiments is further configured to cause display analysis results of historical physiological parameter data of customers associated with a business entity on the business-end terminal. When the analysis results indicate one or more historical physiological parameter is abnormal, the business-end management platform BMP in some embodiments is further configured to cause to display abnormality alert on the business-end terminal. For example, as shown in FIG. 7A, the abnormal parameters are highlighted in bold font. Alternatively, the abnormal parameters may be highlighted in red color.

In the parameter query interface, a person may click on "Detail Report", the business-end management platform in some embodiments is configured to cause to display historical physiological parameter data of a respective customer, e.g., on a new page. In some embodiments, the internet-of-things platform server PS is further configured to analyze historical physiological parameter data of customers associated with a business entity, and generate analysis results. The business server BS is configured to transmit the analysis results to the business-end management platform BMP. In some embodiments, the analysis results include data for visualization of the historical physiological parameter data. The business server BS is configured to transmit the data for visualization of the historical physiological parameter data to the business-end management platform BMP. As shown in FIG. 7B, the business-end management platform BMP is configured to cause to display the data for visualization of the historical physiological parameter data for a respective customer (e.g., the "Trend" curve for fat content over time), on a business-end terminal on which the business-end management platform BMP is loaded.

In some embodiments, the business-end management platform BMP is configured to cause to display an input interface, operable to input personalized medical or nutritional advice for a customer, on a business-end terminal on which the business-end management platform is loaded. FIG. 7C shows a physiological parameter report displayed on the business-end terminal. In some embodiments, the physiological parameter report itself may serve as the input interface. For example, the physiological parameter report (the input interface) contains a space for inputting medical/nutritional advice. The medical/nutritional personnel may directly enter the medical/nutritional advice into this space. The medical/nutritional personnel may review the historical medical/nutritional advice saved in the system. Upon reviewing the historical medical/nutritional advice, the medical/nutritional personnel may better advice the customer in subsequent visits.

In some embodiments, the business server BS is configured to sync the personalized medical or nutritional advice to the physiological parameter data analysis platform and the customer-end personal data management platform.

In some embodiments, the business-end management platform BMP is configured to cause to display a customer query interface on a business-end terminal BT on which the business-end management platform BMP is loaded, operable to query customer information of customers associated with a business entity BS. For example, the customer query interface may be used to view customers' profiles, ranges of ages, levels of education, occupation, regions they are residing, and how many child or children they have. These customer information is helpful for the business entity in optimizing their operation strategy. The business entity may also filter the customer information of customers associated with a business entity BS, making it easy for generate statistics information.

In some embodiments, the business-end management platform BMP is configured to cause to display a business query interface on a business-end terminal on which the business-end management platform is loaded, operable to query operation information of a business entity. The business entity may use business query interface to perform data analysis and operational reports to obtain a clear picture of their daily operation. In one example, the business query interface may be used to view the cumulative revenue of breast milk testing service, newly added customers for each day, cumulative number of customers, and the growth trend of breast milk testing services. In another example, the business query interface may be used to view a selected business entity's daily testing schedule and daily traffic flow in the business entity. In another example, the business query interface may be used for marketing such as sales, discount, holiday specials, etc.

Referring to FIG. 6 again, the internet-of-things platform server PS is further configured to apply big data analysis on historical physiological parameter data stored on the internet-of-things platform server PS, and generate population classification data classifying the population into sub-populations respectively having similar physiological parameter profiles. The business server BS is configured to transmit the population classification data to the customer-end personal data management platform CDP. In some embodiments, the customer-end personal data management platform CDP is configured to cause to display a sub-population classification corresponding to the individual customer's physiological parameter profile on a customer terminal CT on which the customer-end personal data management platform CDP is loaded. This allows the customer to conveniently view how many other customers having physiological parameter profiles (e.g., breast milk contents) that are similar to hers.

In some embodiments, the internet-of-things platform server PS is further configured to generate medical or nutritional advice for a respective sub-population having a respective similar physiological parameter profile. The business server BS is configured to transmit the medical or nutritional advice to the customer-end personal data management platform CDP. In some embodiments, the customer-end personal data management platform CDP is configured to cause to display the medical or nutritional advice on the customer terminal CT. One example of the medical or nutritional advice is dietary recommendations, for example, recipes for a week's meals. The customers can improve their diet based on the recipes for a week's meals. Next time when the customer has her physiological parameter data tested, the customer can evaluate whether the dietary recommendations help improve their condition, e.g., improve milk contents.

In some embodiments, the customer-end personal data management platform CDP is configured to cause to associate the individual customer's account with a community forum targeting a respective sub-population having a respective physiological parameter profile similar to the individual customer's physiological parameter profile, the community forum allowing the individual customer to interact with members of the community forum. For example, the customers may discuss their experience at the business entity, and how the medical or nutritional advice improve their conditions. The customers may also view and comment on other customers' posts, or give a "like" on other customers' posts. Moreover, the customers may also follow tags related to baby health.

In some embodiments, the customer-end personal data management platform CDP is configured to cause to display medical or nutritional knowledge data on a customer terminal on which the customer-end personal data management platform is loaded. In particular, the customers may view certain medical or nutritional knowledge data provided by experts. In another example, the customer-end personal data management platform CDP may push personalized contents to the customers. For example, the personalized contents may include knowledge on how to raise babies in a more scientific manner. In another example, the personalized contents may include parenting knowledge corresponding to each stage of the baby growth. The customer-end personal data management platform CDP may further allow the customers to get points by participating in social media interaction.

In some embodiments, the customer-end personal data management platform CDP is configured to cause to display a reservation interface, operable to reserve an appointment for the point-of-care physiological parameter data collection. Moreover, the reservation interface is operable to allow the customer to cancel an appointment.

In some embodiments, the customer-end personal data management platform CDP is configured to cause to display a ranking interface, operable to allow the individual customer to rank service provided by the business entity hosting the point-of-care physiological parameter data collection.

In some embodiments, the customer-end personal data management platform CDP is configured to allow the individual customer's account to access an online shop for purchasing merchandise.

Various appropriate implementations may be practiced in the present intelligent healthcare management system according to the present disclosure. Each of the physiological parameter data analysis platform DAP, the business-end management platform BMP, the customer-end personal data management platform CDP in some embodiments may be implemented as any of an application (e.g., a mobile application), an installation-free applet, or a software-as-a-service. Optionally, the physiological parameter data analysis platform DAP is implemented as a mobile application, the business-end management platform BMP is implemented as a software-as-a-service, and the customer-end personal data management platform CDP is implemented as an installation-free applet.

In the present intelligent healthcare management system, the distributed computing system includes one or more networked computers configured to execute in parallel to perform at least one common task (e.g., data analysis, data management, data storage, etc.). The intelligent healthcare management system may further include additional on-premise devices (e.g., the user terminal, the business-end terminal, the customer terminal, the internet-of-things physiological parameter data detector, etc.). A respective on-premise device may include a memory; one or more processors; wherein the memory and the one or more processors are connected with each other. The memory stores computer-executable instructions for controlling the one or more processors to perform various on-premise tasks.

Figure 8:
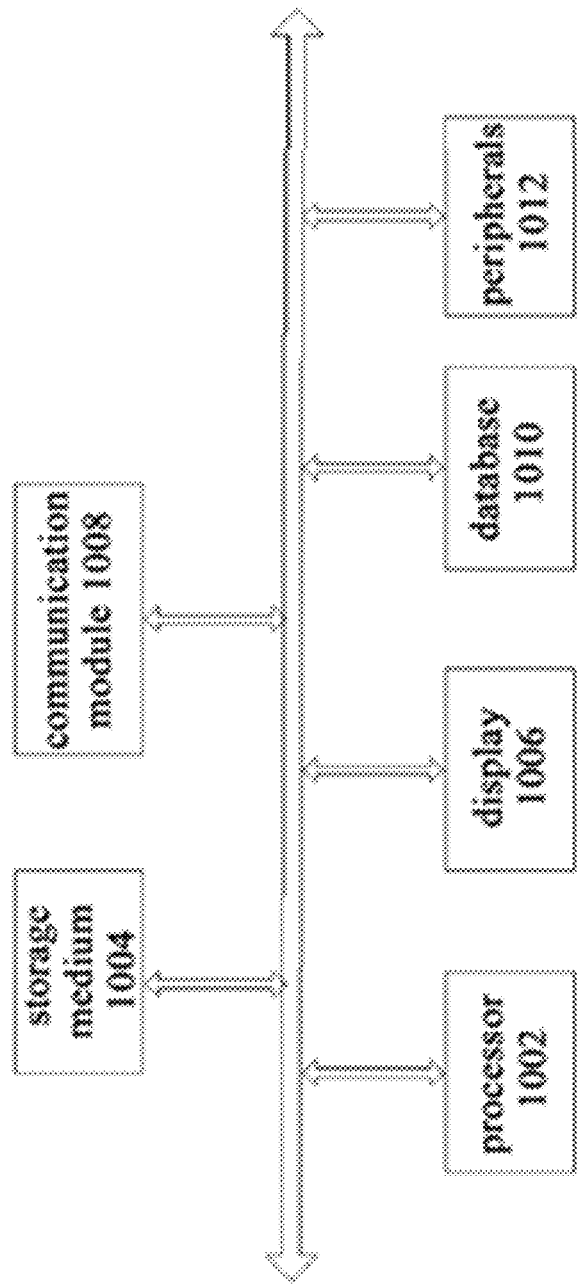
FIG. 8 is a block diagram of an apparatus in some embodiments according to the present disclosure.

FIG. 8 is a block diagram of an apparatus in some embodiments according to the present disclosure. Referring to FIG. 8, in some embodiments, the apparatus 1000 may include any appropriate type of TV, such as a plasma TV, a liquid crystal display (LCD) TV, a touch screen TV, a projection TV, a non-smart TV, a smart TV, etc. The apparatus 1000 may also include other computing systems, such as a personal computer (PC), a tablet or mobile computer, or a smart phone, etc. In addition, the apparatus 1000 may be any appropriate content-presentation device capable of presenting any appropriate content. Users may interact with the dynamic volumetric display apparatus 1000 to perform other activities of interest.

As shown in FIG. 8, the apparatus 1000 may include a processor 1002, a storage medium 1004, a display 1006, a communication module 1008, a database 1010 and peripherals 1012. Certain devices may be omitted and other devices may be included to better describe the relevant embodiments.

The processor 1002 may include any appropriate processor or processors. Further, the processor 1002 may include multiple cores for multi-thread or parallel processing. The processor 1002 may execute sequences of computer program instructions to perform various processes. The storage medium 1004 may include memory modules, such as ROM, RAM, flash memory modules, and mass storages, such as CD-ROM and hard disk, etc. The storage medium 1004 may store computer programs for implementing various processes when the computer programs are executed by the processor 1002. For example, the storage medium 1004 may store computer programs for implementing various algorithms when the computer programs are executed by the processor 1002.

Further, the communication module 1008 may include certain network interface devices for establishing connections through communication networks, such as TV cable network, wireless network, internet, etc. The database 1010 may include one or more databases for storing certain data and for performing certain operations on the stored data, such as database searching.

The display 1006 may provide information to users. The display 1006 may include any appropriate type of computer display device or electronic apparatus display such as LCD or OLED based devices. The peripherals 112 may include various sensors and other IO devices, such as keyboard and mouse.

It will be understood by one of ordinary skill in the art that all or some of steps of the method, functional modules/units in the system and the device disclosed above may be implemented as software, firmware, hardware, or suitable combinations thereof. In a hardware implementation, a division among functional modules/units mentioned in the above description does not necessarily correspond to the division among physical components. For example, one physical component may have a plurality of functions, or one function or step may be performed by several physical components in cooperation. Some or all of the physical components may be implemented as software executed by a processor, such as a central processing unit, a digital signal processor, or a microprocessor, or as hardware, or as an integrated circuit, such as an application specific integrated circuit. Such software may be distributed on a computer-readable storage medium, which may include a computer storage medium (or a non-transitory medium) and a communication medium (or a transitory medium). The term computer storage medium includes volatile and nonvolatile, removable and non-removable media implemented in any method or technology for storage of information, such as computer readable instructions, data structures, program modules or other data, as is well known to one of ordinary skill in the art. A computer storage medium includes, but is not limited to, RAM, ROM, EEPROM, flash memory or other memory technology, CD-ROM, Digital Versatile Disk (DVD) or other optical disk storage, magnetic cassette, magnetic tape, magnetic disk storage or other magnetic storage device, or any other medium which may be used to store desired information and which may accessed by a computer. In addition, a communication medium typically embodies computer readable instructions, data structures, program modules or other data in a modulated data signal such as a carrier wave or other transport mechanism, and includes any information delivery medium, as is well known to one of ordinary skill in the art.

The flowchart and block diagrams in the drawings illustrate architecture, functionality, and operation of possible implementations of a device, a method and a computer program product according to various embodiments of the present disclosure. In this regard, each block in the flowchart or block diagrams may represent a module, program segment(s), or a portion of a code, which includes at least one executable instruction for implementing specified logical function(s). It should also be noted that, in some alternative implementations, functions noted in the blocks may occur out of the order noted in the drawings. For example, two blocks being successively connected may, in fact, be performed substantially concurrently, or the blocks may sometimes be performed in the reverse order, depending upon the functionality involved. It will also be noted that each block of the block diagrams and/or flowchart, and combinations of blocks in the block diagrams and/or flowchart, may be implemented by special purpose hardware-based systems that perform the specified functions or operations, or combinations of special purpose hardware and computer instructions.

In some embodiments, the user terminal is configured to search for the nearby internet-of-things physiological parameter data detector available for pairing; display the unique identification code of the internet-of-things physiological parameter data detector, display the prompt signal requesting connection with the internet-of-things physiological parameter data detector; upon receiving a response signal, establish the connection with the internet-of-things physiological parameter data detector, display the authentication interface, operable to log the user into a user account; and display the physiological parameter detection instructions.

In some embodiments, the user terminal is configured to display a physiological parameter report listing one or more physiological parameters detected by the internet-of-things physiological parameter data detector on the user terminal on which the physiological parameter data analysis platform is loaded; and display a two-dimensional bar code on the user terminal, operable to initiate a file transmission process, upon the two-dimensional bar code being scanned by a customer terminal, transmit the physiological parameter report to the customer terminal In some embodiments, the user terminal is configured to display a query interface, operable to query historical physiological parameter reports of customers associated with an entity.

In some embodiments, the user terminal is configured to display an entity management interface, operable to perform at least one of inputting entity profile of an entity; query upcoming customer reservation information; or video-conference with a customer.

In some embodiments, the business-end terminal is configured to display a parameter query interface, operable to query the historical physiological parameter data of customers associated with a business entity; and display analysis results of historical physiological parameter data of customers associated with a business entity.

In some embodiments, the business-end terminal is configured to display abnormality alert when the analysis results indicate one or more historical physiological parameter is abnormal.

In some embodiments, the business-end terminal is configured to display the data for visualization of the historical physiological parameter data for a respective customer.

In some embodiments, the business-end terminal is configured to display an input interface, operable to input personalized medical or nutritional advice for a customer.

In some embodiments, the business-end terminal is configured to display a customer query interface, operable to query customer information of customers associated with a business entity.

In some embodiments, the business-end terminal is configured to display a business query interface, operable to query operation information of a business entity.

In some embodiments, the customer terminal is configured to display a sub-population classification corresponding to the individual customer's physiological parameter profile.

In some embodiments, the customer terminal is configured to display the medical or nutritional advice.

In some embodiments, the customer terminal is configured to display medical or nutritional knowledge data.

In some embodiments, the customer terminal is configured to display a reservation interface, operable to reserve an appointment for the point-of-care physiological parameter data collection; and/or display a ranking interface, operable to allow the individual customer to rank service provided by the business entity hosting the point-of-care physiological parameter data collection.

The present intelligent healthcare management system integrates service and merchandise sale activity together. Take breast milk testing as an example, the testing service attracts customers to visit the stores. While visiting the stores for the breast milk testing, the customers will browse the merchandise in the stores. Likely at least some customers will also purchase some of the merchandise in the stores, promoting the sales of the stores. The present intelligent healthcare management system also offers great flexibility. The physiological parameter data collection may be performed at a business entity (e.g., a hospital, a health center, a menstrual center) or at the customer's home. The present intelligent healthcare management system allows a customer to initially try it out at the business entity, and take the internet-of-things physiological parameter data detector (e.g., the breast milk analyzer) home for long term use. The present intelligent healthcare management system allows the customer to remotely consult with a medical or nutritional advisor, e.g., through video conferencing.

In another aspect, the present disclosure provides an intelligent healthcare management method. In some embodiments, the intelligent healthcare management method is performed by a distributed computing system comprising one or more networked computers configured to execute in parallel to perform at least one common task (e.g., data analysis, data management, data storage, etc.). In some embodiments, the intelligent healthcare management method includes executing an internet-of-things platform server; executing a business server; executing a physiological parameter data analysis platform configured to provide one or more user interfaces for point-of-care physiological parameter data collection; executing a business-end management platform configured to store and manage historical physiological parameter data of customers associated with a business entity; and executing a customer-end personal data management platform configured to manage personal historical physiological parameter data specific for an individual customer. Optionally, the internet-of-things platform server and the business server are configured to exchange data between each other, the internet-of-things platform server is configured to store and manage physiological parameter data measured by an internet-of-things physiological parameter data detector; and the business server is configured to be in interactive communication with the physiological parameter data analysis platform, the business-end management platform, and the customer-end personal data management platform, respectively.

In some embodiments, the intelligent healthcare management method further includes by executing the physiological parameter data analysis platform, causing a user terminal on which the physiological parameter data analysis platform is loaded to search for a nearby internet-of-things physiological parameter data detector available for pairing with the user terminal; causing to display a unique identification code of the internet-of-things physiological parameter data detector on the user terminal; providing a prompt signal on the user terminal requesting connection between the internet-of-things physiological parameter data detector and the user terminal; causing to display an authentication interface on the user terminal, operable to log a user into a user account; and causing to display a physiological parameter detection instructions on the user terminal.

In some embodiments, the intelligent healthcare management method further includes, by the user terminal, searching for the nearby internet-of-things physiological parameter data detector available for pairing; displaying the unique identification code of the internet-of-things physiological parameter data detector, displaying the prompt signal requesting connection with the internet-of-things physiological parameter data detector; upon receiving a response signal, establishing the connection with the internet-of-things physiological parameter data detector; displaying the authentication interface, operable to log the user into a user account; and displaying the physiological parameter detection instructions.

In some embodiments, the intelligent healthcare management method further includes, by executing the physiological parameter data analysis platform, causing to display a physiological parameter report listing one or more physiological parameters detected by the internet-of-things physiological parameter data detector on a user terminal on which the physiological parameter data analysis platform is loaded, and causing to display a two-dimensional bar code on the user terminal, operable to initiate a file transmission process, upon the two-dimensional bar code being scanned by a customer terminal, transmitting the physiological parameter report to the customer terminal.

In some embodiments, the intelligent healthcare management method further includes, by the user terminal, displaying a physiological parameter report listing one or more physiological parameters detected by the internet-of-things physiological parameter data detector on the user terminal on which the physiological parameter data analysis platform is loaded; and displaying a two-dimensional bar code on the user terminal, operable to initiate a file transmission process, upon the two-dimensional bar code being scanned by a customer terminal, transmitting the physiological parameter report to the customer terminal.

In some embodiments, the intelligent healthcare management method further includes, by executing the physiological parameter data analysis platform, causing to display a query interface, operable to query historical physiological parameter reports of customers associated with an entity.

In some embodiments, the intelligent healthcare management method further includes, by the user terminal, displaying a query interface, operable to query historical physiological parameter reports of customers associated with an entity.

In some embodiments, the intelligent healthcare management method further includes, by executing the physiological parameter data analysis platform, causing to display an entity management interface, operable to perform at least one of inputting entity profile of an entity; querying upcoming customer reservation information; or video-conferencing with a customer.

In some embodiments, the intelligent healthcare management method further includes, by the user terminal, displaying an entity management interface, operable to perform at least one of inputting entity profile of an entity; querying upcoming customer reservation information; or video-conferencing with a customer.

In some embodiments, the intelligent healthcare management method further includes, by executing the business-end management platform, causing to display a parameter query interface on a business-end terminal on which the business-end management platform is loaded, operable to query the historical physiological parameter data of customers associated with a business entity; and causing to display analysis results of historical physiological parameter data of customers associated with a business entity on the business-end terminal.

In some embodiments, the intelligent healthcare management method further includes, by the business-end terminal, displaying a parameter query interface, operable to query the historical physiological parameter data of customers associated with a business entity; and displaying analysis results of historical physiological parameter data of customers associated with a business entity.

In some embodiments, the intelligent healthcare management method further includes, by executing the business-end management platform, causing to display abnormality alert on the business-end terminal when the analysis results indicate one or more historical physiological parameter is abnormal.

In some embodiments, the intelligent healthcare management method further includes, by the business-end terminal, displaying abnormality alert when the analysis results indicate one or more historical physiological parameter is abnormal.

In some embodiments, the intelligent healthcare management method further includes, by executing the internet-of-things platform server, analyzing historical physiological parameter data of customers associated with a business entity, and generating analysis results; and by executing the business server, transmitting the analysis results to the business-end management platform.

In some embodiments, the analysis results comprise data for visualization of the historical physiological parameter data. The intelligent healthcare management method further includes, by executing the business server, transmitting the data for visualization of the historical physiological parameter data to the business-end management platform; and by executing the business-end management platform, causing to display the data for visualization of the historical physiological parameter data for a respective customer, on a business-end terminal on which the business-end management platform is loaded.

In some embodiments, the intelligent healthcare management method further includes, by the business-end terminal, displaying the data for visualization of the historical physiological parameter data for a respective customer.

In some embodiments, the intelligent healthcare management method further includes, by executing the business-end management platform, causing to display an input interface, operable to input personalized medical or nutritional advice for a customer, on a business-end terminal on which the business-end management platform is loaded; and by executing the business server, syncing the personalized medical or nutritional advice to the physiological parameter data analysis platform and the customer-end personal data management platform.

In some embodiments, the intelligent healthcare management method further includes, by the business-end terminal, displaying an input interface, operable to input personalized medical or nutritional advice for a customer.

In some embodiments, the intelligent healthcare management method further includes, by executing the business-end management platform, causing to display a customer query interface on a business-end terminal on which the business-end management platform is loaded, operable to query customer information of customers associated with a business entity.

In some embodiments, the intelligent healthcare management method further includes, by the business-end terminal, displaying a customer query interface, operable to query customer information of customers associated with a business entity.

In some embodiments, the intelligent healthcare management method further includes, by executing the business-end management platform, causing to display a business query interface on a business-end terminal on which the business-end management platform is loaded, operable to query operation information of a business entity.

In some embodiments, the intelligent healthcare management method further includes, by the business-end terminal, displaying a business query interface, operable to query operation information of a business entity.

In some embodiments, the intelligent healthcare management method further includes, by executing the internet-of-things platform server, applying big data analysis on historical physiological parameter data stored on the internet-of-things platform server, and generating population classification data classifying the population into sub-populations respectively having similar physiological parameter profiles; by executing the business server, transmitting the population classification data to the customer-end personal data management platform; and by executing the customer-end personal data management platform, causing to display a sub-population classification corresponding to the individual customer's physiological parameter profile on a customer terminal on which the customer-end personal data management platform is loaded.

In some embodiments, the intelligent healthcare management method further includes, by the customer terminal, displaying a sub-population classification corresponding to the individual customer's physiological parameter profile.

In some embodiments, the intelligent healthcare management method further includes, by executing the internet-of-things platform server, generating medical or nutritional advice for a respective sub-population having a respective similar physiological parameter profile; by executing the business server, transmitting the medical or nutritional advice to the customer-end personal data management platform; and by executing the customer-end personal data management platform, causing to display the medical or nutritional advice on the customer terminal.

In some embodiments, the intelligent healthcare management method further includes, by the customer terminal, displaying the medical or nutritional advice.

In some embodiments, the intelligent healthcare management method further includes, by executing the customer-end personal data management platform, causing to associate the individual customer's account with a community forum targeting a respective sub-population having a respective physiological parameter profile similar to the individual customer's physiological parameter profile, the community forum allowing the individual customer to interact with members of the community forum.

In some embodiments, the intelligent healthcare management method further includes, by executing the customer-end personal data management platform, causing to display medical or nutritional knowledge data on a customer terminal on which the customer-end personal data management platform is loaded.

In some embodiments, the intelligent healthcare management method further includes, by the customer terminal, displaying medical or nutritional knowledge data.

In some embodiments, the intelligent healthcare management method further includes, by executing the customer-end personal data management platform, causing to display a reservation interface, operable to reserve an appointment for the point-of-care physiological parameter data collection; and/or causing to display a ranking interface, operable to allow the individual customer to rank service provided by the business entity hosting the point-of-care physiological parameter data collection.

In some embodiments, the intelligent healthcare management method further includes, by the customer terminal, displaying a reservation interface, operable to reserve an appointment for the point-of-care physiological parameter data collection; and/or displaying a ranking interface, operable to allow the individual customer to rank service provided by the business entity hosting the point-of-care physiological parameter data collection.

In some embodiments, the intelligent healthcare management method further includes, by executing the customer-end personal data management platform, allowing the individual customer's account to access an online shop for purchasing merchandise.

In another aspect, the present disclosure provides a computer-program product for intelligent healthcare management. In some embodiments, the computer-program product includes a non-transitory tangible computer-readable medium having computer-readable instructions thereon. The computer-readable instructions being executable by a processor, in a distributed computing system comprising one or more networked computers configured to execute in parallel to perform at least one common task, to cause the processor to perform executing an internet-of-things platform server; executing a business server; executing a physiological parameter data analysis platform configured to provide one or more user interfaces for point-of-care physiological parameter data collection; executing a business-end management platform configured to store and manage historical physiological parameter data of customers associated with a business entity; and executing a customer-end personal data management platform configured to manage personal historical physiological parameter data specific for an individual customer. Optionally, the internet-of-things platform server and the business server are configured to exchange data between each other; the internet-of-things platform server is configured to store and manage physiological parameter data measured by an internet-of-things physiological parameter data detector; and the business server is configured to be in interactive communication with the physiological parameter data analysis platform, the business-end management platform, and the customer-end personal data management platform, respectively.

In some embodiments, the computer-readable instructions is executable by a processor to cause the processor to perform causing a user terminal on which the physiological parameter data analysis platform is loaded to search for a nearby internet-of-things physiological parameter data detector available for pairing with the user terminal; causing to display a unique identification code of the internet-of-things physiological parameter data detector on the user terminal; providing a prompt signal on the user terminal requesting connection between the internet-of-things physiological parameter data detector and the user terminal; causing to display an authentication interface on the user terminal, operable to log a user into a user account; and causing to display a physiological parameter detection instructions on the user terminal.

In some embodiments, the computer-readable instructions is executable by a processor to cause the processor to perform causing to display a physiological parameter report listing one or more physiological parameters detected by the internet-of-things physiological parameter data detector on a user terminal on which the physiological parameter data analysis platform is loaded; and causing to display a two-dimensional bar code on the user terminal, operable to initiate a file transmission process, upon the two-dimensional bar code being scanned by a customer terminal, transmitting the physiological parameter report to the customer terminal.

In some embodiments, the computer-readable instructions is executable by a processor to cause the processor to perform causing to display a query interface, operable to query historical physiological parameter reports of customers associated with an entity.

In some embodiments, the computer-readable instructions is executable by a processor to cause the processor to perform causing to display an entity management interface, operable to perform at least one of inputting entity profile of an entity; querying upcoming customer reservation information; or video-conferencing with a customer.

In some embodiments, the computer-readable instructions is executable by a processor to cause the processor to perform causing to display a parameter query interface on a business-end terminal on which the business-end management platform is loaded, operable to query the historical physiological parameter data of customers associated with a business entity; and causing to display analysis results of historical physiological parameter data of customers associated with a business entity on the business-end terminal.

In some embodiments, the computer-readable instructions is executable by a processor to cause the processor to perform causing to display abnormality alert on the business-end terminal when the analysis results indicate one or more historical physiological parameter is abnormal.

In some embodiments, the computer-readable instructions is executable by a processor to cause the processor to perform analyzing historical physiological parameter data of customers associated with a business entity, and generating analysis results; and transmitting the analysis results to the business-end management platform.

In some embodiments, the analysis results comprise data for visualization of the historical physiological parameter data. The computer-readable instructions is executable by a processor to cause the processor to perform transmitting the data for visualization of the historical physiological parameter data to the business-end management platform; and causing to display the data for visualization of the historical physiological parameter data for a respective customer, on a business-end terminal on which the business-end management platform is loaded.

In some embodiments, computer-readable instructions is executable by a processor to cause the processor to perform causing to display an input interface, operable to input personalized medical or nutritional advice for a customer, on a business-end terminal on which the business-end management platform is loaded; and syncing the personalized medical or nutritional advice to the physiological parameter data analysis platform and the customer-end personal data management platform.

In some embodiments, computer-readable instructions is executable by a processor to cause the processor to perform causing to display a customer query interface on a business-end terminal on which the business-end management platform is loaded, operable to query customer information of customers associated with a business entity.

In some embodiments, computer-readable instructions is executable by a processor to cause the processor to perform causing to display a business query interface on a business-end terminal on which the business-end management platform is loaded, operable to query operation information of a business entity.

In some embodiments, computer-readable instructions is executable by a processor to cause the processor to perform applying big data analysis on historical physiological parameter data stored on the internet-of-things platform server; generating population classification data classifying the population into sub-populations respectively having similar physiological parameter profiles; transmitting the population classification data to the customer-end personal data management platform; and causing to display a sub-population classification corresponding to the individual customer's physiological parameter profile on a customer terminal on which the customer-end personal data management platform is loaded.

In some embodiments, computer-readable instructions is executable by a processor to cause the processor to perform generating medical or nutritional advice for a respective sub-population having a respective similar physiological parameter profile; transmitting the medical or nutritional advice to the customer-end personal data management platform; and causing to display the medical or nutritional advice on the customer terminal.

In some embodiments, computer-readable instructions is executable by a processor to cause the processor to perform causing to associate the individual customer's account with a community forum targeting a respective sub-population having a respective physiological parameter profile similar to the individual customer's physiological parameter profile, the community forum allowing the individual customer to interact with members of the community forum.

In some embodiments, computer-readable instructions is executable by a processor to cause the processor to perform causing to display medical or nutritional knowledge data on a customer terminal on which the customer-end personal data management platform is loaded.

In some embodiments, computer-readable instructions is executable by a processor to cause the processor to perform causing to display a reservation interface, operable to reserve an appointment for the point-of-care physiological parameter data collection; and/or causing to display a ranking interface, operable to allow the individual customer to rank service provided by the business entity hosting the point-of-care physiological parameter data collection.

In some embodiments, computer-readable instructions is executable by a processor to cause the processor to perform allowing the individual customer's account to access an online shop for purchasing merchandise.

Various illustrative operations described in connection with the configurations disclosed herein may be implemented as electronic hardware, computer software, or combinations of both. Such operations may be implemented or performed with a general purpose processor, a digital signal processor (DSP), an ASIC or ASSP, an FPGA or other programmable logic device, discrete gate or transistor logic, discrete hardware components, or any combination thereof designed to produce the configuration as disclosed herein. For example, such a configuration may be implemented at least in part as a hard-wired circuit, as a circuit configuration fabricated into an application-specific integrated circuit, or as a firmware program loaded into non-volatile storage or a software program loaded from or into a data storage medium as machine-readable code, such code being instructions executable by an array of logic elements such as a general purpose processor or other digital signal processing unit. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. A software module may reside in a non-transitory storage medium such as RAM (random-access memory), ROM (read-only memory), nonvolatile RAM (NVRAM) such as flash RAM, erasable programmable ROM (EPROM), electrically erasable programmable ROM (EEPROM), registers, hard disk, a removable disk, or a CD-ROM; or in any other form of storage medium known in the art. An illustrative storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The foregoing description of the embodiments of the invention has been presented for purposes of illustration and description. It is not intended to be exhaustive or to limit the invention to the precise form or to exemplary embodiments disclosed. Accordingly, the foregoing description should be regarded as illustrative rather than restrictive. Obviously, many modifications and variations will be apparent to practitioners skilled in this art. The embodiments are chosen and described in order to explain the principles of the invention and its best mode practical application, thereby to enable persons skilled in the art to understand the invention for various embodiments and with various modifications as are suited to the particular use or implementation contemplated. It is intended that the scope of the invention be defined by the claims appended hereto and their equivalents in which all terms are meant in their broadest reasonable sense unless otherwise indicated. Therefore, the term "the invention", "the present invention" or the like does not necessarily limit the claim scope to a specific embodiment, and the reference to exemplary embodiments of the invention does not imply a limitation on the invention, and no such limitation is to be inferred. The invention is limited only by the spirit and scope of the appended claims. Moreover, these claims may refer to use "first", "second", etc. following with noun or element. Such terms should be understood as a nomenclature and should not be construed as giving the limitation on the number of the elements modified by such nomenclature unless specific number has been given. Any advantages and benefits described may not apply to all embodiments of the invention. It should be appreciated that variations may be made in the embodiments described by persons skilled in the art without departing from the scope of the present invention as defined by the following claims. Moreover, no element and component in the present disclosure is intended to be dedicated to the public regardless of whether the element or component is explicitly recited in the following claims.

What is claimed is:

1. An intelligent healthcare management system, comprising:
   a distributed computing system comprising one or more networked computers configured to execute in parallel to perform at least one common task; and
   one or more computer readable storage mediums storing instructions that, when executed by the distributed computing system, cause the distributed computing system to execute software modules;
   wherein the software modules comprise:
   an internet-of-things platform server;
   a business server;
   a physiological parameter data analysis platform configured to provide one or more user interfaces for point-of-care physiological parameter data collection;
   a business-end management platform configured to store and manage historical physiological parameter data of customers associated with a business entity; and
   a customer-end personal data management platform configured to manage personal historical physiological parameter data specific for an individual customer;
   wherein the internet-of-things platform server and the business server are configured to exchange data between each other;
   the internet-of-things platform server is configured to store and manage physiological parameter data measured by an internet-of-things physiological parameter data detector; and
   the business server is configured to be in interactive communication with the physiological parameter data analysis platform, the business-end management platform, and the customer-end personal data management platform, respectively;
   wherein the customer-end personal data management platform is an applet;
   a customer terminal is configured to load a program package of the applet, and execute the program package;
   the customer terminal is configured to automatically release a resource occupied by the applet after the applet is disabled; and
   the physiological parameter data analysis platform is configured to transmit the physiological parameter data detected by the physiological parameter data analysis platform to the business server, and the business server is configured to transmit the physiological parameter data to the internet-of-things platform server;
   wherein the customer-end personal data management platform is further configured to:
   display medical or nutritional advice generated for a sub-population having a similar physiological parameter profile;
   receive an evaluation from the customer regarding whether the advice helped improve a physiological parameter;
   transmit the evaluation to the internet-of-things platform server for incorporation into ongoing big data analysis;
   display a time-series visualization of historical physiological parameter data for the customer on the customer terminal;
   overlay medical or nutritional advice corresponding to time points along the time-series visualization, thereby enabling the customer to observe physiological trends in relation to advice history; and
   display a statistical comparison interface that shows the customer's physiological parameter values relative to reference ranges and statistical distributions from a sub-population classification, thereby enabling the customer to benchmark her data against that of similar individuals.

2. The intelligent healthcare management system of claim 1, wherein the physiological parameter data analysis platform is configured to:

cause a user terminal on which the physiological parameter data analysis platform is loaded to search for a nearby internet-of-things physiological parameter data detector available for pairing with the user terminal;

cause to display a unique identification code of the internet-of-things physiological parameter data detector on the user terminal;

provide a prompt signal on the user terminal requesting connection between the internet-of-things physiological parameter data detector and the user terminal;

cause to display an authentication interface on the user terminal, operable to log a user into a user account; and cause to display a physiological parameter detection instructions on the user terminal.

3. The intelligent healthcare management system of claim 1, wherein the physiological parameter data analysis platform is configured to:

cause to display a physiological parameter report listing one or more physiological parameters detected by the internet-of-things physiological parameter data detector on a user terminal on which the physiological parameter data analysis platform is loaded; and cause to display a two-dimensional bar code on the user terminal, operable to initiate a file transmission process, upon the two-dimensional bar code being scanned by a customer terminal, transmitting the physiological parameter report to the customer terminal.

4. The intelligent healthcare management system of claim 1, wherein the physiological parameter data analysis platform is configured to:

cause to display a query interface, operable to query historical physiological parameter reports of customers associated with an entity.

5. The intelligent healthcare management system of claim 1, wherein the physiological parameter data analysis platform is configured to:

cause to display an entity management interface, operable to perform at least one of:

inputting entity profile of an entity;

querying upcoming customer reservation information; or video-conferencing with a customer.

6. The intelligent healthcare management system of claim 2, further comprising the internet-of-things physiological parameter data detector, and the user terminal;

wherein the user terminal is configured to:

search for the nearby internet-of-things physiological parameter data detector available for pairing;

display the unique identification code of the internet-of-things physiological parameter data detector;

display the prompt signal requesting connection with the internet-of-things physiological parameter data detector;

upon receiving a response signal, establish the connection with the internet-of-things physiological parameter data detector;

display the authentication interface, operable to log the user into a user account; and display the physiological parameter detection instructions.

7. The intelligent healthcare management system of claim 1, wherein the business-end management platform is configured to:

cause to display a parameter query interface on a business-end terminal on which the business-end management platform is loaded, operable to query the historical physiological parameter data of customers associated with a business entity; and cause to display analysis results of historical physiological parameter data of customers associated with a business entity on the business-end terminal.

8. The intelligent healthcare management system of claim 7, wherein the business-end management platform is configured to cause to display abnormality alert on the business-end terminal when the analysis results indicate one or more historical physiological parameter is abnormal.

9. The intelligent healthcare management system of claim 1, wherein the internet-of-things platform server is further configured to analyze historical physiological parameter data of customers associated with a business entity, and generate analysis results; and the business server is configured to transmit the analysis results to the business-end management platform.

10. The intelligent healthcare management system of claim 7, wherein the analysis results comprise data for visualization of the historical physiological parameter data;

wherein the business server is configured to transmit the data for visualization of the historical physiological parameter data to the business-end management platform; and wherein the business-end management platform is configured to cause to display the data for visualization of the historical physiological parameter data for a respective customer, on a business-end terminal on which the business-end management platform is loaded.

11. The intelligent healthcare management system of claim 1, wherein the business-end management platform is configured to:

cause to display an input interface, operable to input personalized medical or nutritional advice for a customer, on a business-end terminal on which the business-end management platform is loaded;

wherein the business server is configured to sync the personalized medical or nutritional advice to the physiological parameter data analysis platform and the customer-end personal data management platform.

12. The intelligent healthcare management system of claim 1, wherein the business-end management platform is configured to:

cause to display a customer query interface on a business-end terminal on which the business-end management platform is loaded, operable to query customer information of customers associated with a business entity.

13. The intelligent healthcare management system of claim 1, wherein the business-end management platform is configured to:

cause to display a business query interface on a business-end terminal on which the business-end management platform is loaded, operable to query operation information of a business entity.

14. The intelligent healthcare management system of claim 1, wherein the internet-of-things platform server is further configured to apply big data analysis on historical physiological parameter data stored on the internet-of-things platform server, and generate population classification data classifying the population into sub-populations respectively having similar physiological parameter profiles;

wherein the business server is configured to transmit the population classification data to the customer-end personal data management platform; and wherein the customer-end personal data management platform is configured to cause to display a sub-population classification corresponding to the individual customer's physiological parameter profile on a customer terminal on which the customer-end personal data management platform is loaded.

15. The intelligent healthcare management system of claim 14, wherein the internet-of-things platform server is further configured to generate medical or nutritional advice for a respective sub-population having a respective similar physiological parameter profile;
wherein the business server is configured to transmit the medical or nutritional advice to the customer-end personal data management platform; and
wherein the customer-end personal data management platform is configured to cause to display the medical or nutritional advice on the customer terminal.

16. The intelligent healthcare management system of claim 14, wherein the customer-end personal data management platform is configured to:
cause to associate the individual customer's account with a community forum targeting a respective sub-population having a respective physiological parameter profile similar to the individual customer's physiological parameter profile, the community forum allowing the individual customer to interact with members of the community forum.

17. The intelligent healthcare management system of claim 1, wherein the customer-end personal data management platform is configured to:
cause to display medical or nutritional knowledge data on a customer terminal on which the customer-end personal data management platform is loaded.

18. The intelligent healthcare management system of claim 1, wherein the customer-end personal data management platform is configured to:
cause to display a reservation interface, operable to reserve an appointment for the point-of-care physiological parameter data collection; and/or
cause to display a ranking interface, operable to allow the individual customer to rank service provided by the business entity hosting the point-of-care physiological parameter data collection.

19. An intelligent healthcare management method performed by a distributed computing system comprising one or more networked computers configured to execute in parallel to perform at least one common task;
the method comprising:
executing an internet-of-things platform server;
executing a business server;
executing a physiological parameter data analysis platform configured to provide one or more user interfaces for point-of-care physiological parameter data collection;
executing a business-end management platform configured to store and manage historical physiological parameter data of customers associated with a business entity; and
executing a customer-end personal data management platform configured to manage personal historical physiological parameter data specific for an individual customer;
wherein the internet-of-things platform server and the business server are configured to exchange data between each other;
the internet-of-things platform server is configured to store and manage physiological parameter data measured by an internet-of-things physiological parameter data detector; and
the business server is configured to be in interactive communication with the physiological parameter data analysis platform, the business-end management platform, and the customer-end personal data management platform, respectively;
wherein the customer-end personal data management platform is an applet;
a customer terminal is configured to load a program package of the applet, and execute the program package;
the customer terminal is configured to automatically release a resource occupied by the applet after the applet is disabled; and
the physiological parameter data analysis platform is configured to transmit the physiological parameter data detected by the physiological parameter data analysis platform to the business server, and the business server is configured to transmit the physiological parameter data to the internet-of-things platform server;
wherein the customer-end personal data management platform is further configured to:
display medical or nutritional advice generated for a sub-population having a similar physiological parameter profile;
receive an evaluation from the customer regarding whether the advice helped improve a physiological parameter;
transmit the evaluation to the internet-of-things platform server for incorporation into ongoing big data analysis;
display a time-series visualization of historical physiological parameter data for the customer on the customer terminal;
overlay medical or nutritional advice corresponding to time points along the time-series visualization, thereby enabling the customer to observe physiological trends in relation to advice history; and
display a statistical comparison interface that shows the customer's physiological parameter values relative to reference ranges and statistical distributions from a sub-population classification, thereby enabling the customer to benchmark her data against that of similar individuals.

20. A computer-program product, for intelligent healthcare management, comprising a non-transitory tangible computer-readable medium having computer-readable instructions thereon, the computer-readable instructions being executable by a processor, in a distributed computing system comprising one or more networked computers configured to execute in parallel to perform at least one common task, to cause the processor to perform:
executing an internet-of-things platform server;
executing a business server;
executing a physiological parameter data analysis platform configured to provide one or more user interfaces for point-of-care physiological parameter data collection;
executing a business-end management platform configured to store and manage historical physiological parameter data of customers associated with a business entity; and
executing a customer-end personal data management platform configured to manage personal historical physiological parameter data specific for an individual customer;
wherein the internet-of-things platform server and the business server are configured to exchange data between each other;

the internet-of-things platform server is configured to store and manage physiological parameter data measured by an internet-of-things physiological parameter data detector; and the business server is configured to be in interactive communication with the physiological parameter data analysis platform, the business-end management platform, and the customer-end personal data management platform, respectively;

wherein the customer-end personal data management platform is an applet;

a customer terminal is configured to load a program package of the applet, and execute the program package;

the customer terminal is configured to automatically release a resource occupied by the applet after the applet is disabled; and the physiological parameter data analysis platform is configured to transmit the physiological parameter data detected by the physiological parameter data analysis platform to the business server, and the business server is configured to transmit the physiological parameter data to the internet-of-things platform server;

wherein the customer-end personal data management platform is further configured to:

display medical or nutritional advice generated for a sub-population having a similar physiological parameter profile;

receive an evaluation from the customer regarding whether the advice helped improve a physiological parameter;

transmit the evaluation to the internet-of-things platform server for incorporation into ongoing big data analysis;

display a time-series visualization of historical physiological parameter data for the customer on the customer terminal;

overlay medical or nutritional advice corresponding to time points along the time-series visualization, thereby enabling the customer to observe physiological trends in relation to advice history; and display a statistical comparison interface that shows the customer's physiological parameter values relative to reference ranges and statistical distributions from a sub-population classification, thereby enabling the customer to benchmark her data against that of similar individuals.

* * * * *